(12) United States Patent
Butt et al.

(10) Patent No.: US 10,982,243 B2
(45) Date of Patent: Apr. 20, 2021

(54) METHODS FOR INCREASING PRODUCTION OF CANNABINOIDS IN YEAST CELLS

(71) Applicant: CB Therapeutics, Inc., Carlsbad, CA (US)

(72) Inventors: Sher Ali Butt, San Diego, CA (US); Jacob Michael Vogan, San Diego, CA (US)

(73) Assignee: CB THERAPEUTICS, INC., Carlsbad, CA (US)

( * ) Notice: Subject to any disclaimer, the term of this patent is extended or adjusted under 35 U.S.C. 154(b) by 0 days.

(21) Appl. No.: 16/553,492

(22) Filed: Aug. 28, 2019

(65) Prior Publication Data

US 2020/0063171 A1 Feb. 27, 2020

Related U.S. Application Data

(63) Continuation of application No. 15/719,430, filed on Sep. 28, 2017, now Pat. No. 10,435,727, which is a continuation of application No. 15/096,164, filed on Apr. 11, 2016, now abandoned.

(60) Provisional application No. 62/145,430, filed on Apr. 9, 2015.

(51) Int. Cl.
| | |
|---|---|
| *C12P 17/06* | (2006.01) |
| *C12P 13/02* | (2006.01) |
| *C12P 7/22* | (2006.01) |
| *C12N 15/52* | (2006.01) |
| *C12P 7/42* | (2006.01) |

(52) U.S. Cl.
CPC .............. *C12P 13/02* (2013.01); *C12N 15/52* (2013.01); *C12P 7/22* (2013.01); *C12P 7/42* (2013.01); *C12P 17/06* (2013.01)

(58) Field of Classification Search
None
See application file for complete search history.

(56) References Cited

U.S. PATENT DOCUMENTS

| | | |
|---|---|---|
| 6,630,507 B1 | 10/2003 | Hampson |
| 7,179,800 B2 | 2/2007 | Martin |
| 8,884,100 B2 | 11/2014 | Page |
| 9,394,510 B2 | 7/2016 | Peet |
| 9,822,384 B2 | 11/2017 | Poulous |
| 2007/0032544 A1 | 2/2007 | Korthout |
| 2008/0031977 A1 | 2/2008 | Musty |
| 2009/0042964 A1 | 2/2009 | Malamas |
| 2009/0042974 A1 | 2/2009 | Parker |
| 2010/0016418 A1 | 1/2010 | Guy |
| 2010/0292345 A1 | 11/2010 | Pertwee |
| 2011/0021617 A1 | 1/2011 | Korthout |
| 2011/0098348 A1 | 4/2011 | DeMeijer |
| 2012/0144523 A1 | 6/2012 | Page |
| 2015/0128301 A1 | 5/2015 | Page |
| 2016/0010126 A1 | 1/2016 | Poulos |
| 2020/0063170 A1* | 2/2020 | Butt ........................ C12P 13/02 |
| 2020/0063171 A1* | 2/2020 | Butt ........................ C12P 7/22 |

FOREIGN PATENT DOCUMENTS

| | | |
|---|---|---|
| WO | WO2011017798 A1 | 2/2011 |
| WO | WO2016010827 A1 | 1/2016 |

OTHER PUBLICATIONS

Taura, F. Studies on tetrahydrocannabinolic acid synthase that produces the acidic precursor of tetrahydrocannabinol, the pharmacologically active cannabinoid in marijuana. Drug Discov Ther. 2009; 3(3):83-87.

Taura, F. et al. Purification and Characterization of Cannabidiolic-acid Synthase from *Cannabis sativa* L.: Biochemical Analysis of a Novel Enzyme That Catalyzes the Oxidocyclization of Cannabigerolic Acid to Cannabidiolic Acid. J. Biol. Chem. 1996; 271: 17411-17416.

Taura. F el al. Cannabidiolic-acid synthase, the chemotype-determining enzyme in the fiber-type Cannabis sativa. FEBS Letters. 2007; 581: 2929-2934.

Fellermeier M. et al. Biosynthesis of cannabinoids: Incorporation experiments with 13C-labeled glucose. Eur. J. Biochem. 2008; 268: 1596-1064.

Fellermeier, M. et al. Prenylation of olivetolate by a hemp transferase yields cannabigerolic acid, the precursor of tetrahydrocannabinol. FEBS Letters. 1998; 427: 283-285.

Nevoigt, E. Progress in metabolic engineering of *Saccharomyces cerevisiae*. Microbiology and Molecule Biology Reviews. 2009; 72: 378-412.

Flores-Sanchez, I.J. et al. Secondary metabolism in cannabis. Phytochem Rev. 2008; 7: 615-639.

(Continued)

*Primary Examiner* — Hope A Robinson
(74) *Attorney, Agent, or Firm* — Torrey Pines Law Group, PC

(57) ABSTRACT

The present invention is a method for the biosynthesis of hundreds of compounds, mainly found in the *cannabis* plant. The starting material for these compounds can be any biological compound that is used/produced in a biological organism from the sugar family starting materials or other low cost raw materials processed via enzymes or within organisms to give final products. These final products include, but are not limited to: cannabinoids, terpenoids, stilbenoids, flavonoids, phenolic amides, lignanamides, spermidine alkaloids, and phenylpropanoids. Specifically, the present invention relates to the regular, modified, or synthetic gene(s) of select enzymes that are processed and inserted into an expression system (for example, a vector, cosmid, BAC, YAC, phage) to produce modified hosts. The modified host is then optimized for efficient production and yield via manipulation, silencing, and amplifying inserted or other genes in the host, leading to an efficient system for product.

10 Claims, 8 Drawing Sheets
Specification includes a Sequence Listing.

(56) References Cited

OTHER PUBLICATIONS

Eisenreich, W. et al. The deoxyxylulose phosphate pathway of terpenoid biosynthesis in plants and microorganisms. Chemistry & Biology. 1998; 5: R221-R233.

Gagne, S.J. et al. Identification of olivetolic acid from Cannabis sativa reveals a unique catalytic route to plant polyketides, PNAS, 2012, 109: 12811-12816.

* cited by examiner (Genetic Modifications of Genes in our Pathway for Accelerated High Yield Development)

MVA Pathway

Alternative HMG-CoA Pathway for Leucine Catabolism

METHODS FOR INCREASING PRODUCTION OF CANNABINOIDS IN YEAST CELLS

CROSS-REFERENCE TO RELATED APPLICATIONS

The present application is a continuation of U.S. Ser. No. 15/719,430, filed on Sep. 28, 2017 entitled "An Isolated Codon Optimized Nucleic Acid" and issued as U.S. Pat. No. 10,435,727 on Oct. 8, 2019, which is a continuation of U.S. Ser. No. 15/096,164, filed Apr. 11, 2016, entitled "A Novel Method for the Cheap, Efficient, and Effective Production of Pharmaceutical and Therapeutic API's, Intermediate, and Final Products", that claims the benefit of U.S. Provisional Patent Application Ser. No. 62/145,430, entitled "A Novel Method for the Cheap, Efficient, and Effective Production of Pharmaceutical and Therapeutic API's, Intermediate, and Final Products", filed Apr. 9, 2015, all of which are herein incorporated by reference in their entirety for all purposes.

The Sequence Listing, which is a part of U.S. Ser. No. 15/719,430, filed on Sep. 28, 2017 entitled "An Isolated Codon Optimized Nucleic Acid", includes a computer readable form and a written sequence listing comprising nucleotide and/or amino acid sequences of the present application. The sequence listing information recorded in computer readable form is identical to the written sequence listing. The ASCII text file, entitled "SeqListIsolatedCodonSequenceC2.txt" was created on Oct. 27, 2019 using Patent In version 3.5 and is incorporated herein by reference in its entirety. The subject matter of the Sequence Listing is incorporated herein by reference in its entirety.

FIELD OF INVENTION

The present invention is in the technical field of large scale production of pharmaceutical and supplemental products for various common illnesses, medical conditions, and general industrial use. More particularly, the present invention is in the technical field of bio-synthesis of cannabinoids, terpenoids, stilbenoids, flavonoids, phenolic amides, lignanamides, spermidine alkaloids, and phenylpropanoids; compounds found in *Cannabis sativa*, along with various combinations and specialized formulations which are beneficial in ailments ranging from cancer to glaucoma. The final product(s) can be an intermediate or a compound of interest. The core concept of the invention is based on the idea of cheaper and more efficient production, along with novel products and applications.

Introduction

Cannabinoids from *cannabis* have been used for thousands of years for treatment of various ailments and conditions in many different cultures around the world. However, most of various types of cannabinoids in *cannabis* are at a very low concentration in the plant. Therefore, most patients/users never get a threshold dosage for any kind of relief from anything other than tetrahydrocannabinolic acid (THC/A), cannabinolic-acid (CBD/A), and cannabinol (CBN). There are a few strains or concentrates available that have a rare cannabinoid, but are usually very highly concentrated in tetrahydrocannabinol (THC) or cannabidiol (CBD) to have any pronounced effect by the rare cannabinoid.

In other words, the pharmaceutical industry has not tapped into the real potential of the *cannabis* plant. With time, more research is being conducted into the different kinds of cannabinoids and their medicinal applications. Researchers are finding that many of the other cannabinoids also have unique medicinal properties.

SUMMARY

Biosynthesis of important molecules can be used for therapeutic applications, bulk substance production, intermediate API biosynthesis, and various other novel formulations and applications for such substances, as known to those skilled in the art. Many biological molecules can be changed/converted into molecules of importance by using enzymes and other processes. This process can be utilized by employing methods for transforming a range of starting materials into final products to be used in pharmaceuticals and supplements as active ingredients, or donating a significant portion of their structure to the final active ingredients. The final products can also be used in other industries and applications, such as food, beverage, and other goods production. For example, table sugar, starch, and cellulose can be converted to glucose, creating a molecule that can readily be utilized by any organism as an energy source. Therefore, depending on the specific compound(s) being manufactured, and the kind(s) of starting materials available, along with the host and production technique(s) any kind of host engineering, various expression systems and methods, and varying materials, a spectrum of different methods and products is possible.

The advantages of the present invention include, without limitation, creation of hundreds of compounds from readily available biological molecules that can be produced and harvested from virtually all known sources of plants and other energy producing organisms. Since sugar producing plants and organisms, biomass, and carbon based industrial waste products are very abundant, our "raw material" will be very cheap and easy to obtain anywhere in the world. After scaling up the given methods, hundreds of compounds with medicinal properties can be produced at a very low cost, allowing the widespread distribution and aiding of millions of people.

Another advantage is that there is no need or use of growing any illegal plants. For example, no marijuana, poppy, or other plant production is necessary. This is advantageous as it will lead to drastically cutting down the production, consumption, and trafficking of many unregulated substances.

The most important advantage of the present invention is that we can make and use many compounds that are virtually so low in concentration in the *cannabis* plant, that there is no effect in using *cannabis* if we are only after the therapeutic effects of these compounds. For example, patients using marijuana can only benefit from tetrahydrocannabinolic acic (THCA), THC, cannabidiolic acid (CBDA), CBD, CBN, and a few other compound class families, as the concentrations of the other compounds is so low that it has no effect. This invention will allow the production of hundreds of compounds in pure form, leading to many new medical discoveries and applications.

BRIEF DESCRIPTION OF THE FIGURES

The nature, objects, and advantages of the present invention will become more apparent to those skilled in the art after considering the following detailed description in con

DETAILED DESCRIPTION

Figure 1:
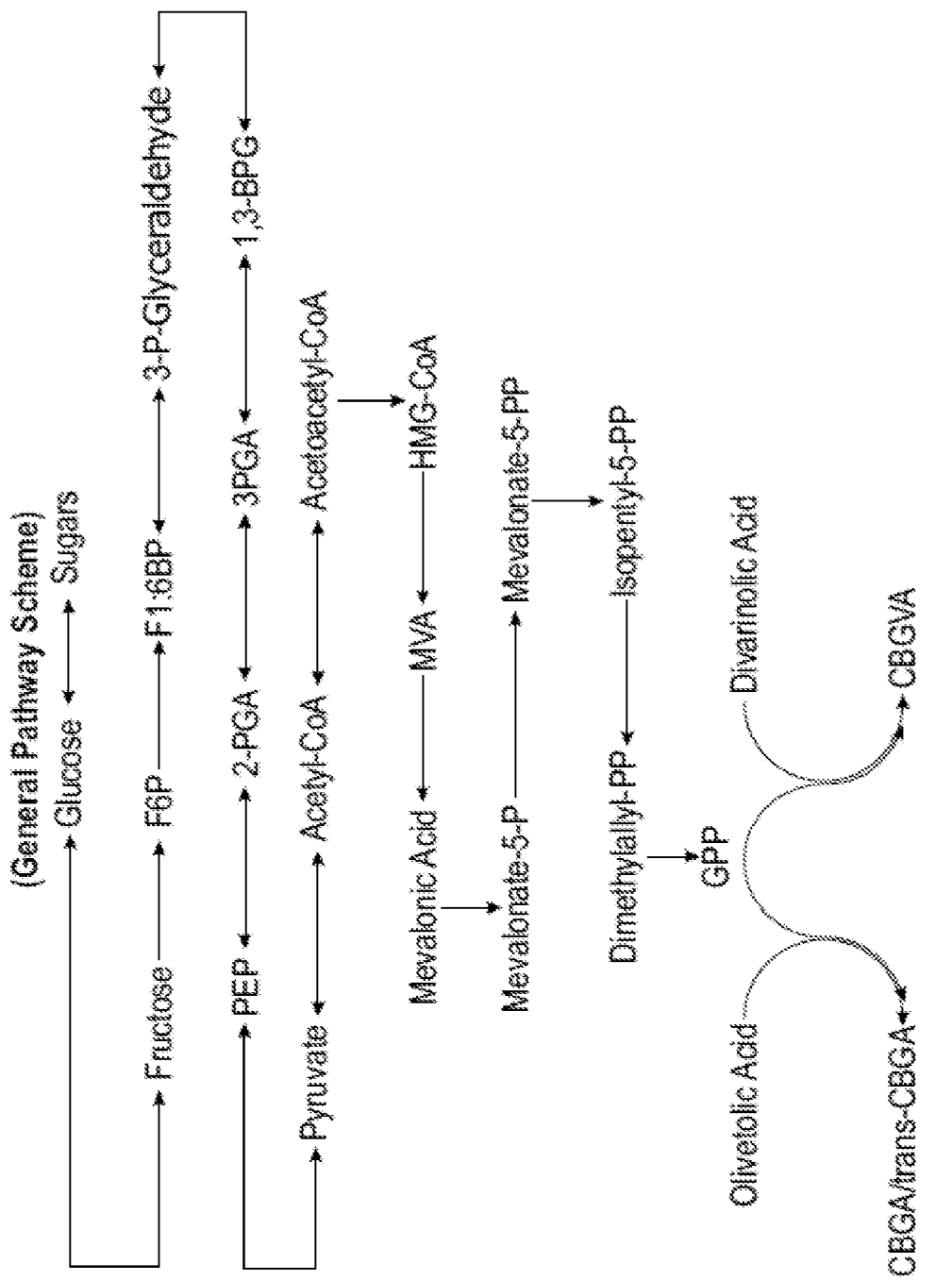
- FIG. 1 is a diagram of the pathway for the biosynthesis of all molecules of interest via the conversion of starting materials to glucose and then to final products.

The present invention is a method for the biosynthesis of hundreds of compounds, mainly found in the *cannabis* plant. The starting material for these compounds can be any biological compound that is used/produced in a biological organism from the sugar family starting materials or other low cost raw materials processed via enzymes or within organisms to give final products. These final products include, but are not limited to: cannabinoids, terpenoids, stilbenoids, flavonoids, phenolic amides, lignanamides, spermidine alkaloids, and phenylpropanoids (collectively, "final products").

Definitions, Terms, Elements

The Following are a List and their Definitions:

Genetic engineering: targeted manipulation of a cell's genetic information;

Rational Metabolic Engineering: engineering of enzymes, transporters, or regulatory proteins based on available information about enzymes, pathways, and their regulation.

Evolutionary engineering: encompasses all methods for empirical strain improvement (mutagenesis [natural or induced] and recombination and/or shuffling of genes, pathways, and even whole cells; usually performed in cycles or sequentially Cannabinoids: compounds that are terpenophenolic with 22 carbons (21 carbons for neutral forms), found in *cannabis*

Terpenoids: also known as isoprenoids, class of organic compounds

Stilbenoids: hydroxylated derivatives of stilbene

Flavonoids/phenylpropanoids: compounds derived from or using phenylalanine as a precursor Lignanamides/phenolic amides: compounds produced through tyramine pathways Spermidine alkaloids: compounds produced through glutamic acid pathways Starting material/reactant/excipient: compounds used for the initial step of biosynthesis, which are cheap and readily available Intermediate: products that are formed within the biosynthesis pathways, which can further be processed to make final products, or can, themselves, be utilized as a final product Final product/product/end product/compounds of interest: cannabinoids, terpenoids, stilbenoids, flavonoids, phenolic amides, lignanamides, spermidine alkaloids, and phenylpropanoids In-vivo: inside the cell In-vitro: outside the cell BAC: bacterial artificial chromosome, carrier of DNA of interest into host YAC: yeast artificial chromosome, carrier of DNA of interest into host Vector/cosmid/phage: carrier of DNA of interest into host Starting Materials All biological organisms produce organic molecules that are processed in many different processes in the organism. The present invention utilizes starting materials that are either:

1) Readily available and relatively pure
2) Cheap to produce or buy
3) Easily modified (via enzymes, catalysts, or other methods)

Based on the above criteria, there are multiple groups and families of compounds that would fit one or all three of the above criteria. These groups and families of compounds include, but are not limited to: ligno-cellulosic biomass, forest biomass, energy/food production waste, but are not limited to: ligno-cellulosic biomass, forest biomass, energy/food production waste, commonly available sugar-based substrates, food and feed grains.

Sugars and metabolic intermediates from cellular processes can be used as starting materials. Sugars can be found in abundance in many substances, including, but not limited to the following: rice, soya/rape, cereals (maize), wheat, beans, sugar beet (sugar cane), plant biomass (wood), grasses, and various other sources. Starch, cellulose, fructose, ethanol, and saccharose in the aforementioned substances can be enzymatically converted to glucose, which, after filtration and purification steps, can be used as a raw material for the final products.

Subsequent steps can also be performed on the lignocellulose, which further makes hemicellulose and cellulose, both which make glucose. An advantage of this method is that there are by-products generated which can be sold as raw material to make hydrocarbons, biogas, and other fuel sources. Whole crops or parts of crops, or waste matter from crop products can be used and incorporated into this system, yielding an "eco-friendly" facility. Products made from these raw materials can use any of the starting materials listed in Table 2.

Within the realm of readily available non-biomass/crop bulk material, HFCS (high fructose corn syrup) is a cost effective syrup made with fruit sources that contains anywhere from 30-90% fructose, along with some other sugars. Plants that make molasses, HFCS, and other sugars can be genetically modified to enhance the production of sugar, leading to better yields of starting material from the crop. Other products from these plants can also be incorporated into compounds of interest production via slight system modification. Biodiesel, ethanol, glycerol, lactic acid, whey and glucose are a few others. These work due to the fact that any of these products can be converted into starting material for our own purposes using enzymatic or physiochemical tools.

Plants also have their own innate levels of metabolites that can be harvested into the process from a plant biomass source. Processes can be crafted that utilize most of the metabolites and biomass for API production giving the maximum efficiency and usability per amount of starting material used. (Enzyme combinations or chambers that utilize most intermediates, sugars, oils, etc. in each biomass load).

Biorefineries can be custom designed that cater to specific raw material (plant biomass for harvesting lignocellulose which is further processed and refined into a simple carbohydrate used in the API manufacturing processes). During certain steps throughout the process, thermochemical and other processing can be used for higher efficiencies which are not possible with biochemical processing alone.

Another group of cheap starting materials is agricultural residue, grass, aquatic biomass, and water hyacinth. Products such as oils and alcohols can be made with these bulk materials. These materials can be converted enzymatically and chemically into starting materials that can readily by injected into our API production system.

Specifically, biorefineries can be designed to be extremely efficient, using all parts of the raw material. For example, concerning plant biomass, the biomass can be step-wise processed so we are able to harvest all individual components. The first step can be using solvent to extract terpenes, alkaloids, etc. Other methods can be used to extract steroids, triglycerides, and other valuable metabolites. Finally the biomass can be treated with cellulases to give glucose, which is one of the primary raw materials of choice.

Production Roadmap Summary

The present invention is a method that covers the biosynthesis of hundreds of compounds, mainly found in the *cannabis* plant. The starting material for these compounds can be any biological compound that is used/produced in a biological organism from the sugar family starting materials or other low cost raw materials processed via enzymes or within organisms to give final products. Information related to the starting materials were detailed in the previous section.

Most sugars and related compounds can be inter-changed using various enzyme systems. For example, we can convert glucose to fructose using Fructose 6-Phosphate (F-6-P) as an intermediate.

Apart from starting materials, we can either:

1) Make enzymes via vectors in bacteria (e.g. *E. coli*) or yeast (e.g. *S. cerevisiae*), extract enzymes, and create in vitro models for making cannabinoids.

2) Make enzymes via protein synthesizing systems (Protein Synth. Robot, Cell Free Expression Systems, etc.)

3) Make final products (compounds of interest) in bacteria or yeast via vectors, plasmids, cosmids, mRNA, various RNA, etc; feed them substrate and purify product.

4) Genetically engineer strains of bacteria and yeast that specialize in cannabinoid production, or intermediate production, or substrate production, etc.

5) Use organic chemistry for certain parts of the above processes.

6) Use various plant starting material for large quantities of substrates or intermediates.

7) Genetically engineer various plants to produce cannabinoids. (e.g. Tomatoes or celery that naturally produce cannabinoids, or algae that produces cannabinoids)

8) Using bioengineered or unengineered *C. sativa* or any other plant/algae cell lines for enzyme/substrate/intermediates/product(s) production.

9) Protein engineering on the various proteins involved in the processes; engineering will enhance the functionality, ruggedness, and efficiency of the enzymes, and altering them into a novel protein, one not found to be covered in any of the above prior art patents.

10) Genetically engineer various plant species to produce higher yielding raw material (sugars) to be used in production of the products. A possibility is to have an indoor/grow for different plants to be used as raw material producers.

After the final product is made, a purification system will filter and concentrate the target molecules. Examples include large scale filtration systems such as chromatography. Once a pure product, we can utilize liquid solutions, caps, sprays, and other delivery systems.

As many of these final products are made, their applications can be seen from glaucoma to cancer, or general well-being. Certain cofactors can be combined with certain final products for more efficacy against specific medical conditions (e.g. combine certain vitamins or other therapeutic compounds with certain compounds of interest). We can also make final products that have certain combinations of compounds of interest with other cofactors as well (e.g. combine THCA/CBDA/Vitamin C, or CBDVA/CBD). This patent covers all the products above and also ones discovered in the future based on the same principles and methods.

DETAILED DESCRIPTION OF THE FIGURES

Referring now to the invention in more detail, in FIG. 1 there is shown a family of sugars and other common derivatives. Along each arrow for each reaction, the number denotes a specific enzyme that catalyzes the reaction. Starting with any sugar in FIG. 1 (list of starting materials in Table 1), we can convert it to glucose to incorporate it into the reaction using the appropriate enzyme, as known to those skilled in the art. An unlimited number of ways are possible when dealing with any starting material, as described above. Enzymes needed for each kind of substrate can be made in vivo or in vitro just as we will be doing for the enzymes in the final product or intermediate production. The final sugar that enters our mechanism will be either glucose or fructose. Through the glycolysis pathway, the sugar will be converted into Acetyl-CoA with the addition of ATP and CoA (shown in FIG. 1). From this point on, the intermediate can follow a variety of paths that can lead to hundreds of products. There are many alternative ways of doing this. We can use the DOX, MEP or MVA pathways to get isopentenyl pyrophosphate (IPP) and DMAPP, which give us geranyl diphosphate (GPP) and NPP. For a reaction with Olivetolic Acid or Divarinolic Acid, we get many cannabinoids as final products.

Figure 2:
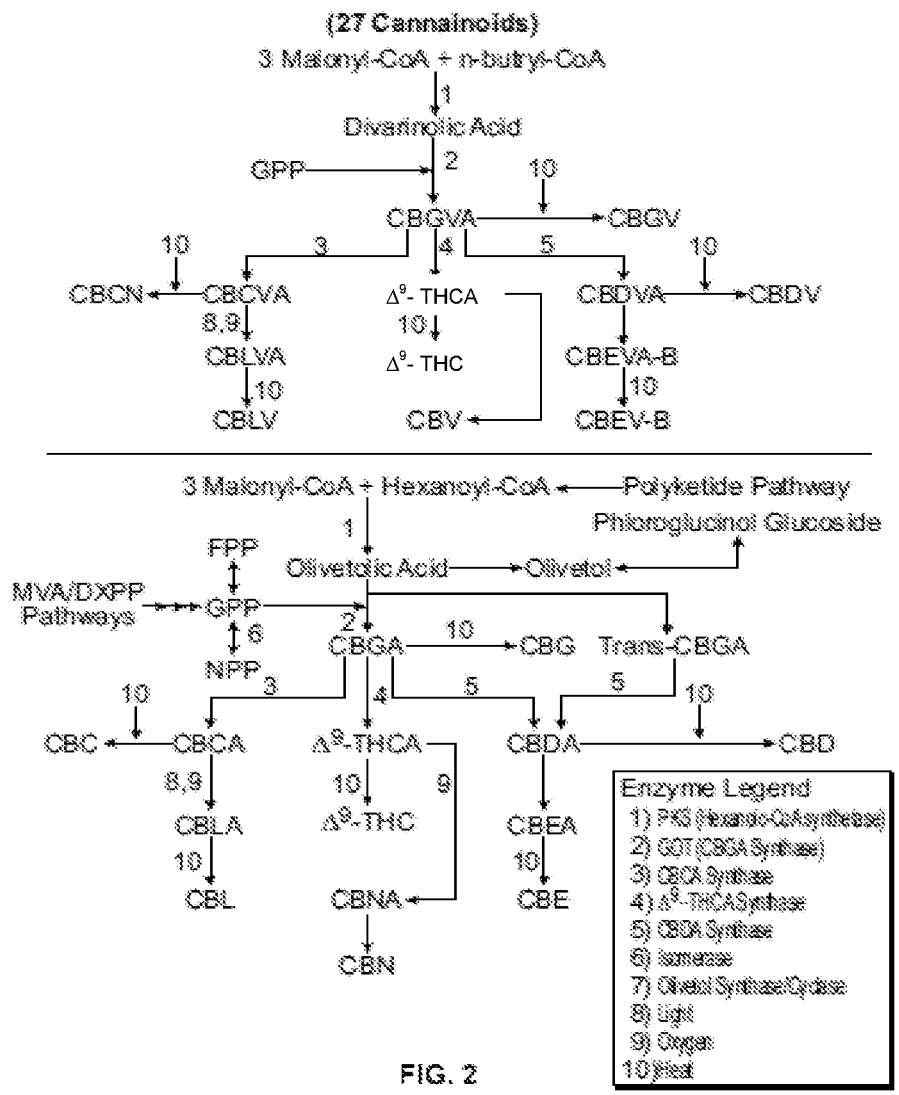
FIG. 2 is a diagram of the pathway for the biosynthesis of cannabinoids.

The generalized pathway for the production of cannabinoids once the starting material is converted to glucose is the following, using appropriate enzymes as known by those skilled in the art:

Glucose→Fructose→F-6-P→F1:6BP→3-P-Glyceraldehyde→1,3-BPG63PGA→2-PGA→PEP→Pyruvate→Acetyl-CoA→Acetoacetyl CoA→HMG-CoA→M-VA→Mevalonic Acid→Mevalonate-5-P→Mevalonate-5-PP→Isopentyl-5-PP→Dimethylallyl-PP→NPP/GPP→GPP This general pathway is outlined in FIG. 1. From this point on, the pathway can utilize Olivetolic Acid or Divarinolic Acid with GPP, yielding CBGA or CBGVA, which can further yield other cannabinoids, as shown in FIG. 2.

Figure 3:
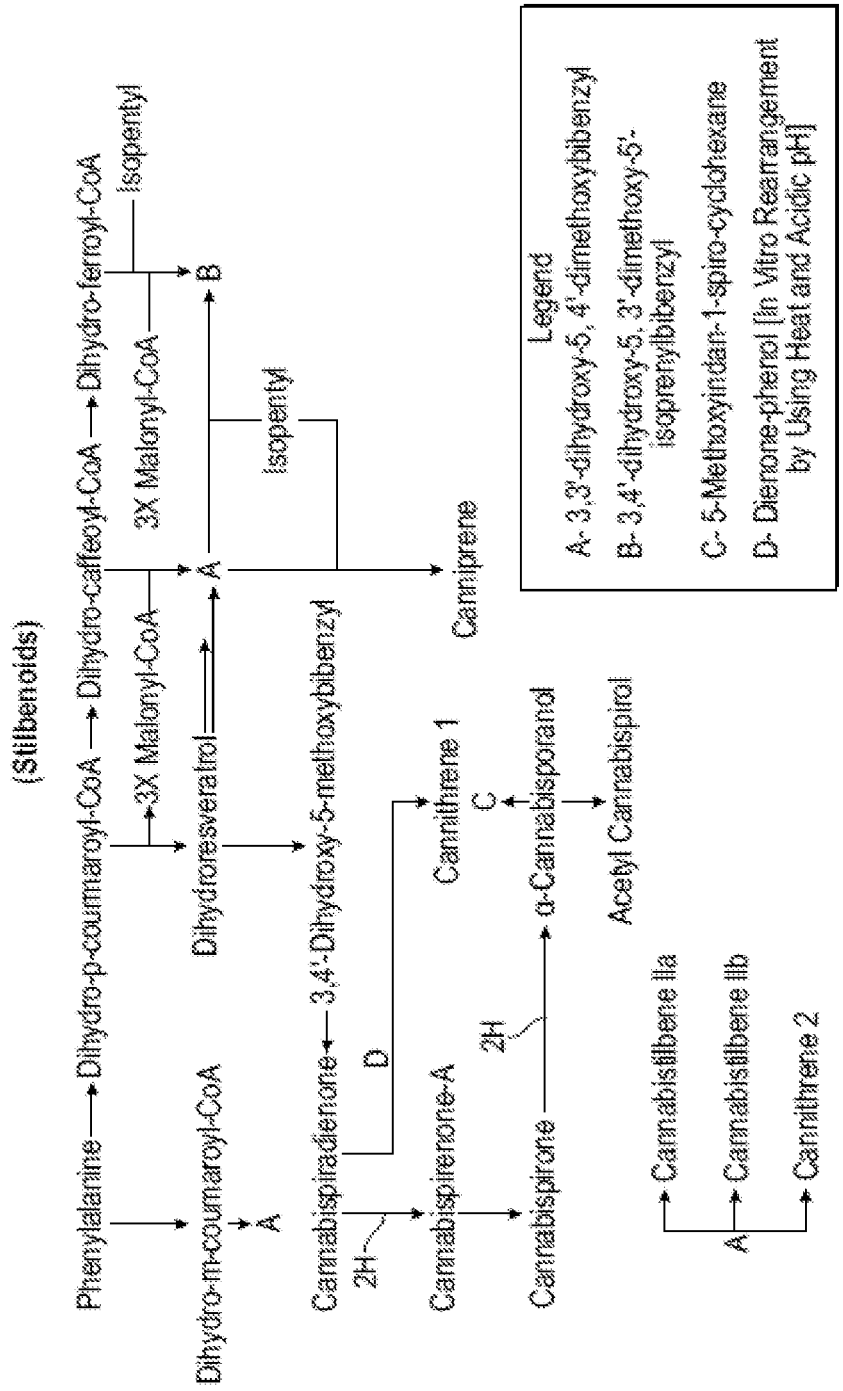
FIG. 3 is a diagram of the pathway for the biosynthesis of stilbenoids.
Figure 4:
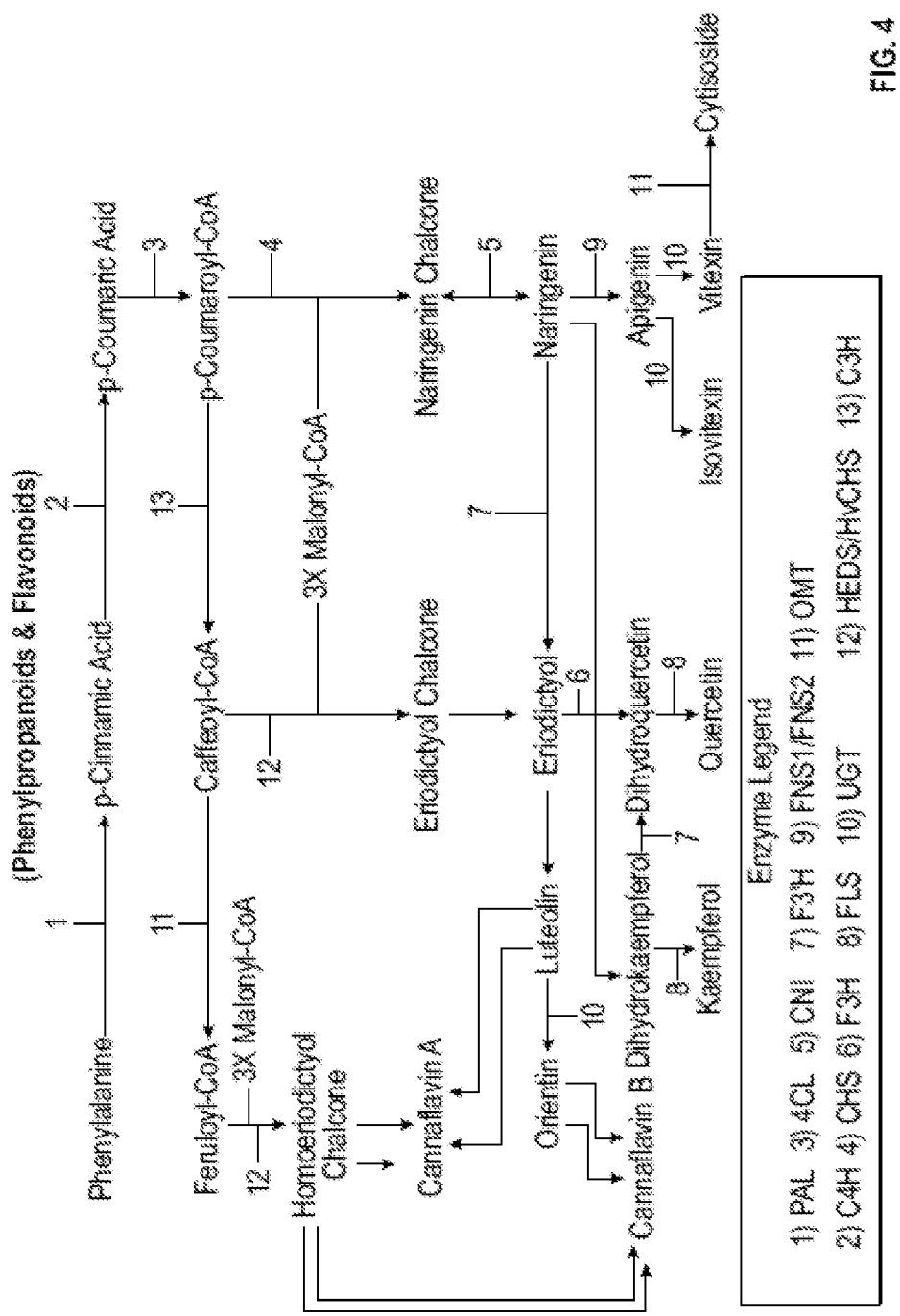
FIG. 4 is a diagram of the pathway for the biosynthesis of phenylpropanoids and flavonoids.

The pathways for stilbenoids, phenylpropanoids, and flavonoids work in a similar fashion. Phenylalanine is generated from sugars, which is then further processed into other compounds using enzymes to final compounds, as shown in FIG. 3 and FIG. 4.

Figure 5:
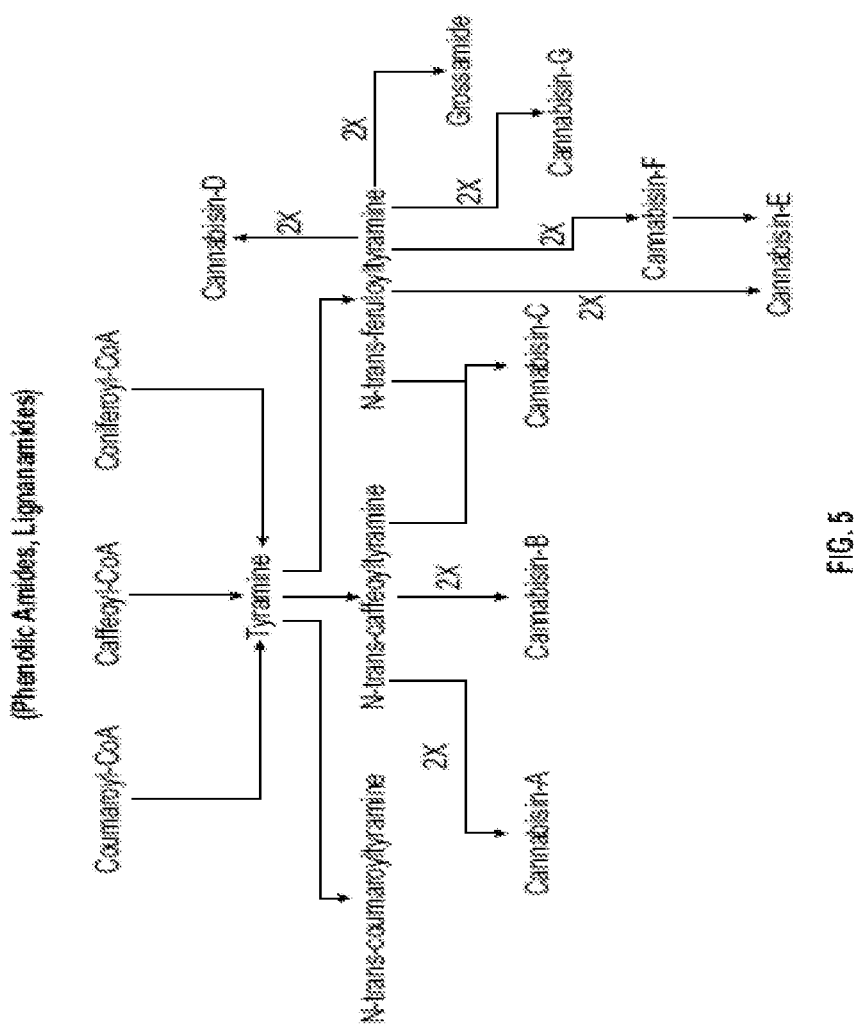
FIG. 5 is a diagram of the pathway for the biosynthesis of phenolic amides andligananamides.
Figure 6:
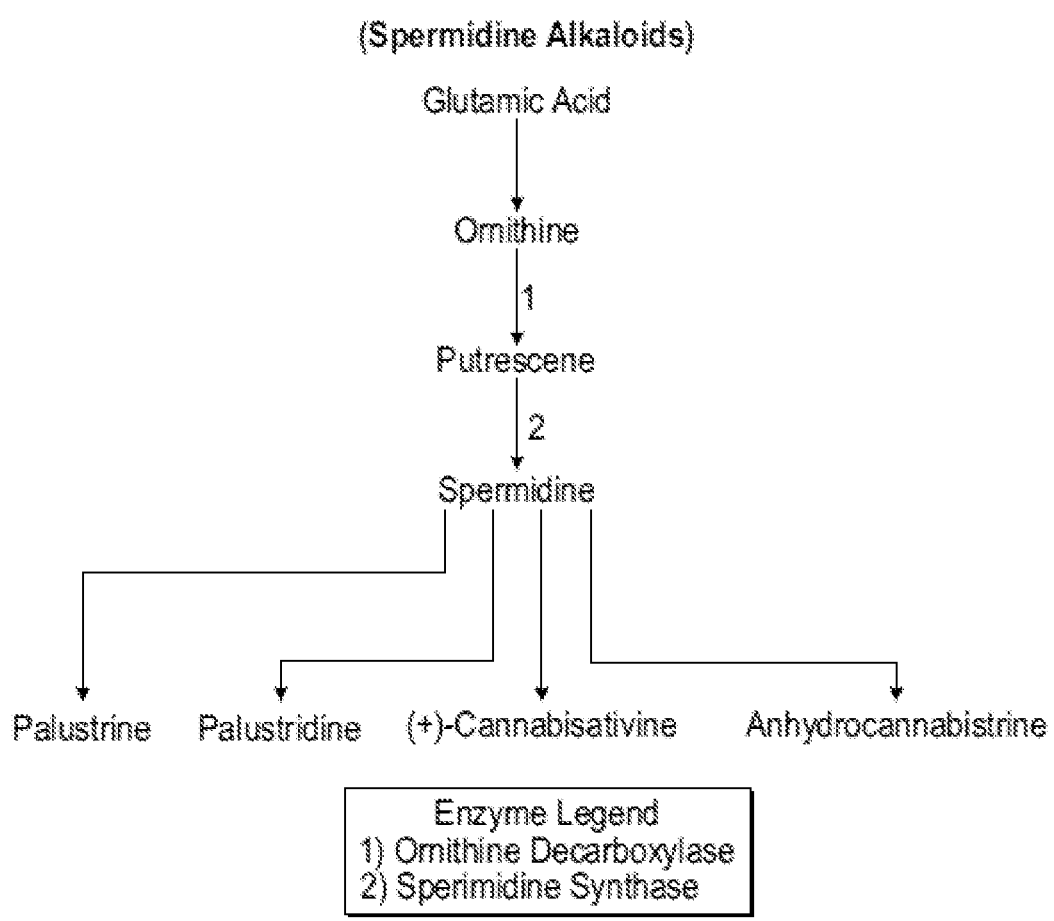
FIG. 6 is a diagram of the pathway for the biosynthesis of spermidine alkaloids.

Phenolic amides and lignanamide pathways are derived from tyramine molecules reacting with other compounds, as shown in FIG. 5. Tyramine can also be synthesized in our cells of interest as most living organisms contain the pathway to synthesize tyramine on their own. Same is the case for spermidine alkaloid production, as most cells already produce glutamic acid, which can be further processed by enzymes into the final components, as shown in FIG. 6.

Figure 7:
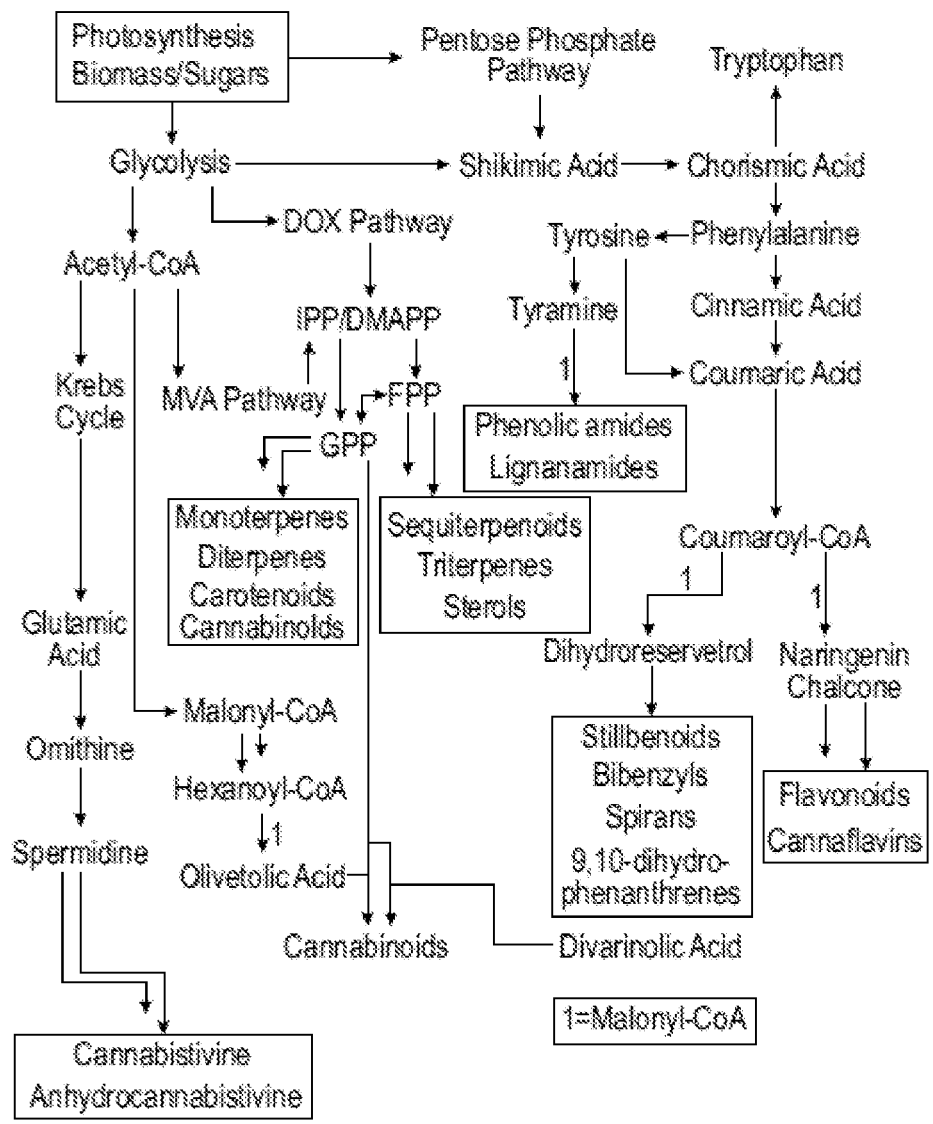
FIG. 7 is a diagram of the combined biosynthetic pathways of FIGS. 1-6.

FIG. 7 is the total pathway overview, showing how all the different classes of compounds can be made, and the general paths they take for being biosynthesized in the cell.

Overview of Procedure

A general scheme of the work flow is as follows:

1) Regular/modified/synthetic gene(s) of select enzymes are processed and inserted into an expression system (vector, cosmid, BAC, YAC, phage, etc.) to produce modified hosts.

2) Mod host is then optimized for efficient production and yield via manipulation, silencing, and amplifying inserted or other genes in the host, leading to an efficient system for product. It is important to remember that every organism is different, and to get a specific compound each optimization will also be different.

3) Mod host can produce enzymes and final products/intermediates, or be further modified using host engineering techniques. (Host engineering Can also be performed before insertion of exp. System)

4) Mod and engineering hosts produce products and intermediates.

5) Product is purified and can be further modified/processed.

In Table 1, different final products are listed along with possible uses. This list is by no means exhaustive, and as such this patent covers any molecules that are made this way. Table 2 lists all possible starting materials that can be utilized for a cheap and efficient biosynthesis.

In more detail, referring to the inter-conversion of sugars, we employ enzymes readily available in the market. Pure enzyme stock can be diluted and added to a solution with the substrates. Once the reaction is complete, we can filter out the enzyme via dialysis tubing, by precipitation out of the solution, chromatography, or other industrial methods for filtration and purification. Each step in FIGS. 1 to 7 will give work with this strategy, leading us up to the final products or key intermediate molecules. Certain steps in the process can be worked on by using chemical and physical methods as well. For example, prenylation of certain compounds can be done outside the cell, as it may be advantageous to do so since unprenylated compounds are also high value compounds. Small batches can be prenylated accordingly to demand via a chemical process.

There are also commercially available cell free expression systems, which are able to produce proteins without the need of any host. With appropriate optimization steps, it is possible to get a cheap and efficient process for production of these compounds using identified starting molecules.

Application Techniques

Referring to bacterial, yeast, plant, and algae incorporation of genes, there are a number of strategies that can be applied to achieve this. We can:

1) Add genes for 1-10 enzymes in various commercially available vectors, cosmids, plasmids, etc. Only need 1-10 enzymes added, as others are already built in most living organisms. For example, glycolysis pathway and related enzymes are already present in most hosts.

2) Bioengineer genes for better yield and suitability in the host.

3) Bioengineer strains of bacteria and yeast that are specialized in producing important molecules. Many metabolic strategies exist, with identification by appropriate screening methods:

1) Rational metabolic engineering: engineering pathways using available information 2) Evolutionary engineering: using random genetic perturbations and/or mutations (via random mutagenesis in whole genome and/or parts)

3) Transposon mutagenesis & gene overexpression libraries: overexpression and/or deletion of single or multiple genes;

4) Global transcription machinery engineering: basal transcription factors mutagenesis causing a global reprogramming of gene transcription and/or translation One strategy is to suppress any pathway that is not essential to our goals or the survival of the host. Another is to enhance our key pathways, or mixing and matching the two methods. The second strategy is through rapid directed evolution, possible by producing many generations so eventually we get a generation of host that has evolved with our genes/functions of interest.

4) Bioengineer custom basic life forms that are specifically making our products, using another organism or using synthetic/modifications. Components from other hosts and system to make a custom organism.

5) Bioengineer bacteria and yeast to have enzyme genes in their chromosomes, and make intermediates or final products inside the host. The product of this process can further be modified.

6) Propagate various colonies of organisms which coexist symbiotically, with the first making our starting material after utilizing a precursor, and the other colonies making our final product. This process can also be incorporated into an ecosystem type setup of different chambers, each holding different organisms that use specific parts of the raw material to produce intermediates or final products that can be modified post-manufacturing.

Referring to the extraction of enzymes once they have been produced in the host, there are many ways to isolate and purify our enzymes. Many organisms have the ability to excrete proteins, which can be collected much easier than cell lysis, as known by those skilled in the art. This technique is the preferred method.

Another method is to lyse the host culture and purify with traditional biochemistry methods (gels, centrifugation, ammonium sulfate precipitation, etc.), use a specialized nickel column with a prep HPLC (need to add a HIS tag to our proteins; remove HIS tag after purification), etc.

Example 1 (Bacterial)

Bacteria (*E. Coli*, etc.) are inserted with exp. system giving us a modified host. The mod host can either be further processed or it can generate products.

Products/intermediates are made in the host, and may be either enzymes that are further extracted and used in vitro, or we add substrates into the bacterial culture so they use the enzymes produced in them to make the substrate. Either way (protein or prod production), purification is carried out to get final products, or intermediates that can be further processed in vitro to give final products. Throughout this procedure, host engineering can be carried out at any step of any process to get better yields.

Example 2 (Plants)

Plant tissue can be used as a starting material to get a tissue culture going. Appropriate expression vectors/systems carry our interest genes into the cells. Alternatively, cell engineering can lead to many combinations that may have similar or different outcomes. The culture can be grown into full plants, and products are ingested by consuming the plants (e.g. tomatoes with certain cannabinoids produced within, etc.). The second way uses the cell culture in a synthetic environment to produce final products/intermediates. Finally, product is purified and used.

Example 3 (Algae)

Algae are modified with the usual techniques used for host engineering. Once completed, the mod host can be embedded into a system similar to biofuel production from algae. Using sunlight and some nutrients, the algae produces final products/intermediates, which is appropriately filtered from the bulk. Other products generated can be further processed to get biofuels or other important compounds that can readily be sold in the market.

Example 4 (Fungi)

Fungi modified with the techniques can:
1) Use plastic to produce final products/intermediates. Plastic needs to be processed and broken down into components before being used in this process via chemical and biological processes, known by those skilled in the art.
2) Clean up waste, whilst producing final products/intermediates at the same time.
3) Produce beer and wine with fungi that also makes final prod/intermediates. Beer and wine will contain our compounds of interest.
4) Use fungi cultures to produce compounds of interest.
5) Genes for *S. cerevisiae* strains to be modified for better yields of final products:
tHMGR
upc2-1 (allows higher uptake of exogenous sterol five-fold from medium)
ERG genes (ERG6, ERG2, ERG3, ERG1, ERG11, ERG24, ERG25, ERG9, ERG10, ERG13, ERG12, ERGS, ERG19, ERG20)
HMGR1 and HMGR2
IDI genes
Gal80p
DPP1, ADH2, and ALD6 genes
FPP/GPP synthase (chose avian FPP synthase as it exhibits higher catalytic turnover rates and lower Kms for substrates than other prenyltransferases)

Figure 8:
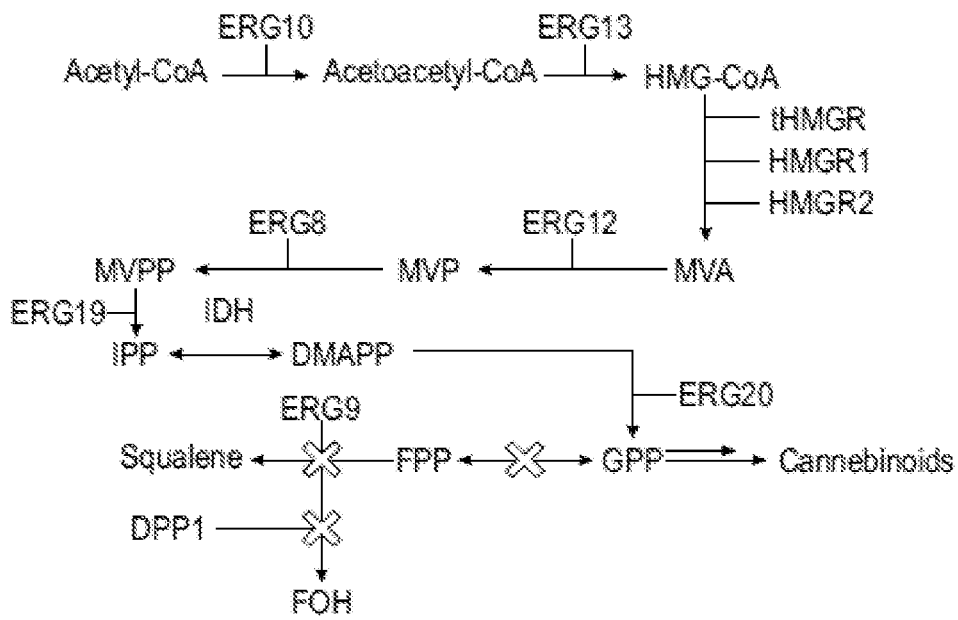
FIG. 8 is diagram of the genetic modification of certain genes for higher product yield in *Saccharomyces cerevisiae* yeast.
Figure 8:
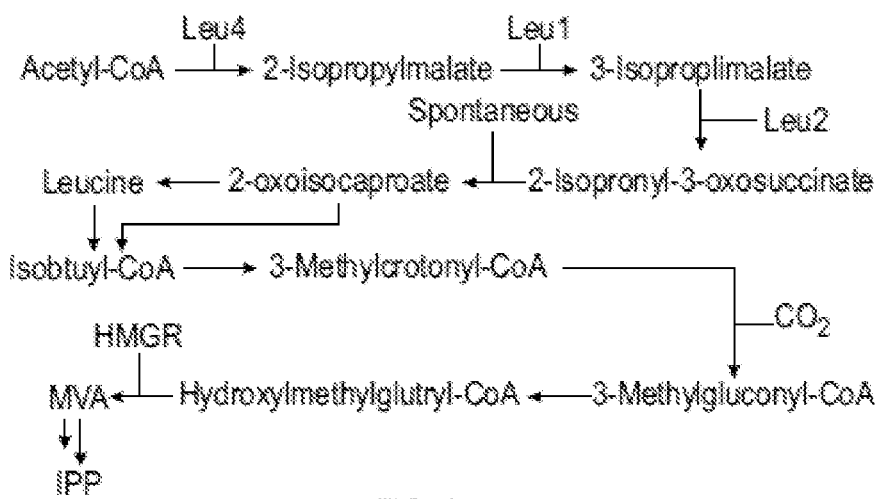

Manipulation, deletion, overexpression, and other modifications to the genes listed above will produce strains that are highly efficient for the production of our compounds of interest. These strains have an exogenous sterol uptake, as the internal sterol pathway has been disabled by manipulations so that all the carbon flux can be directed toward the production of our compounds of interest. Example of genetic pathway regulation in yeast is shown in FIG. 8.

Our initial strategy in *S. cerevisiae* was to increase the carbon flux of our pathways of interest, while decreasing or eliminating pathways that led carbon flux away from our pathways as well. We also focused on exogenous sterol uptake for higher production and secretion levels, cell permeability for more efficient and cheaper production, along with focusing the pathways on utilizing the cheapest sugars. Dynamic control over ergosterol regulation can increase yields as well. Overall result is a strain that is has increased yield many fold, while making the overall production more stable and cheaper.

1) Perform EMS mutagenesis on yeast strains (BY4741, BY4742, CEN.PK, CEN.PK2, EPY300) to get colonies with a SUE (sterol uptake exogenous) mutation. This enables us to provide exogenous sterol to the yeast while cancelling out the gene that diverts carbon flux towards ergosterol, thereby increasing total carbon flux. Without the SUE mutation, the cell diverts lots of carbon flux toward manufacturing sterols, thereby diverting the pools of intermediates away from our compounds and interest leading to very low yields.

2) Perform ERG1 (Squalene monooxygenase) and ERG9 (Squalene synthase) gene knockouts. ERG1 knockout stops the activity of conversion of squalene to squalene epoxide, thereby complementing the SUE mutation and allowing higher uptake of exogenous ergosterol, while ERG9 knockout takes out the cells ability to divert carbon flux towards other metabolites.

3) On some lines, we can perform a DPP1 knockout. DPP1 knockout ensures that isoprenoids farnesyl pyrophosphate (FPP) and GPP are not converted to FOH, thereby blocking the pathway towards FOH products in the cell.

4) Perform ERG2, ERG3, or ERG6 mutations in different cell lines, while performing upregulation mutation on upc2-1 gene (general transcription factor) on all three lines. This helps increase cell membrane permeability for better excretion of our compounds without the need for cell lysis and having the ability to use two-phase or continuous fermentation. This also allows the cells to uptake more fatty acids, thereby increasing the yield many fold.

5) Overexpression of ERG10 (Acetyl-CoA acetyltransferase), ERG13 (Hydroxymethylglutaryl-CoA synthase), HMGR1/2 or tHMGR, ERG12 (Mevalonate kinase), ERGS, IDI1 (Isopentenyl-diphosphate Delta-isomerase 1), HFA1 (Acetyl-CoA carboxylase, mitochondrial) genes in yeast inserted via vectors. By overexpression of these genes, we are amplifying the enzymes of the MVA pathway from the sugars to our compounds, thereby amplifying the intermediates and final products.

6) Modification of avian and/or *salmonella* ERG20 gene encoded FPP synthase (ERG20p). Some cells lines can also be modified using the Erg20p(F96C) mutations. This allows for higher Kms and increased catalytic turnover compared to endogenous GPP synthase, while the engineering itself allows for production of GPP.

7) Gal80p gene deletion so we do not need to use galactose sugar when inducing promoter expression. This is important since others have used galactose promoters, which need expensive galactose sugars for production. By deleting this gene, the cells bypass the need for galactose to express enzymes, leading to cheaper and more efficient biosynthesis.

8) Adding ADH2p promoter to induce strong transcription under conditions with low glucose. This promoter is more efficient than the GAL promoter, and has best results while using non-glucose sugars (ethanol, fructose, etc.) which are cheaper.

9) On some lines, we also overexpress ADH2 and ALD6 genes, along with overexpression of an acetyl-CoA C-acetyltransferase to increase efficiency of the system, while also gaining the ability to convert ethanol to acetate efficiently.

10) Adding and overexpressing enzymes for the production of CBDA (olivetol synthase-olivetolic acid cyclase (OS-OAC) fusion enzyme, CsPti, CBDA Synthase), constructed in a single vector. These enzymes are codon optimized.

11) Grow colonies while adding free fatty acids, and hexanoic acid (for THCA, CBDA, CBGA, CBCA) or butyric acid (for THCVA, CBDVA, CBGVA, CBCVA).

12) For production of THCA/THCVA, use THCA synthase in step 10 instead of CBDA synthase. For production of CBGA/CBGVA, follow step 10 but don't use CBDA synthase in vector construct. For production of CBCA/CBCVA, use CBC synthase in step 10 instead.

Our strategy for *Pichia pastoris* (*Pichia* Pink 1, 2, 3 from Invitrogen) yeast was similar to S. Cerevisiae, except for the following differences:

1) Each enzyme, vector, and primer were optimized for insertion into *pichia* cells instead of S. *cerevisiae*.

2) Methanol is used to supplement cells in addition to free fatty acid, hexanoic acid, and butyric acid, thereby reducing the total cost of production many fold, while eliminating any contamination issues from other species.

3) No EMS mutagenesis is performed.

4) Knockouts of pep4 (encoding Proteinase A), prb1 (encoding Proteinase B), and YPS1 (encoding Aspartic proteinase 3) genes are also introduced. These knockouts allow for the integration of high copy plasmids leading to higher yields.

5) Steps 7, 8, and 9 from the S. *cerevisiae* strategy above are not to be performed in *pichia* cells.

Example 5 (Cell Free Expression Systems)

Vectors are introduced into cell free expression systems, and make either enzymes or intermediate/final products. Further processing or steps are needed to get purified final products.

Procedures
EMS Mutagenesis (S. Cere.; BY4741, BY4742, CEN. PK, CEN. PK2, BY300)

1) Cells incubated overnight @ 30 C in 5 mL TPD medium while shaking @ 200 rpm to establish 200 mL YPD shake flask culture.

2) When OD600 of yeast culture reaches 1.0, cells are spun down by centrifugation (12 mins at 4,000 g), washed twice with 20 mL 0.1M sodium phosphate buffer, pH7.0.

3) Cells concentrated by centrifugation again, re-suspended in 1 mL 0.1M sodium phosphate buffer, transferred to 30 mL FALCON tubes, treated with 300 uL EMS (1.2 g/mL).

4) Cells are incubated at 30 C for 1 hr while shaking.

5) Stop mutagenesis by adding 8 mL of sterile 5% sodium thiosulfate to yeast cells.

6) Cells are pelleted, washed with 8 mL sterile water, concentrated by centrifugation, re-suspended in 1 mL sterile water and 100 uL aliquots plated into YPD-NCS agar plate (YPD+50 mg/L each of cholesterol, nystatin, sqalestatin, and 2% Bacto-agar).

7) In some instances, washed cells were resuspended in 1 mL YPDE liquid media for overnight recovery before plating to YPD-NCS agar medium.

8) Incubate cultures for up to two weeks at 30 C until distinct colonies are visible.

Bacteria & Yeast Culturing

1) Grown using standard culture practices.

2) YPD media without selection consisted of 1% Bacto-yeast extract, 2% Bacto-peptone, and 2% glucose.

3) Add 40 mg/L ergosterol to YPD media to get YPDE media.

4) Add 40 mg/L each of nystatin, cholesterol, and squalestatin to YPD media to get TPDNCS media.

5) Add 40 mg/L each of ergosterol and squalestatin to YPD media to get YPDSE media.

6) Prepare minimal media, SCE (pH5.3), by adding 0.67% Bacto-yeast nitrogen base (without amino acids), 2% dextrose, 0.6% succinic acid, 0.14% Sigma yeast dropout soln (-his, -leu, -ura, -trp), uracil (300 mg/L), L-tryptophan (150 mg/L), L-histidine (250 mg/L), L-methionine (200 mg/L), L-leucine (1 g/L), and 40 mg/L of ergosterol.

7) Cholesterol and ergosterol stocks are 10 mg/mL in 50% Triton X-100, 50% ethanol and kept at −20 C.

8) Selection media prepared similarly except without supplementation of media with indicated reagent based on the yeast auxotrophic markers.

9) All solid media plates are prepared with 2% Bacto-agar.

Yeast Transformation & Culture Performance

1) Used FROZEN-EZ Yeast Transformation II Kit from Zymo Research, Orange, Calif., according to manufacturer's recommendations.

2) 1 ug of plasmid was used per transformation, followed by selection on agar plates of SCE medium lacking specified amino acids for auxotrophic markers, or YPDE containing 300 mg/L hygromycin B for screening erg9 knockout at 30 C.

3) Colonies are picked and used to start 3 mL cultures in minimal media to characterize their terpene production capabilities. (6 days incubation at 30 C while shaking)

4) Best cultures are chosen to move further, using 30 mL shake flask cultures.

5) Cultures are grown to saturation in minimal media, inoculated into 30 mL SCE media and 1 mL aliquots are taken out daily for 15 days.

6) Cell growth is monitored via change in optical density at 600 nm every two days using dilutions at later stages of growth.

7) Production of terpenes is determined via testing.

ERG9 Knockout Mutations

1) Primers ERG9PS1 and ERG9-250downS2 used to amplify hygromycin resistance gene, hphNT1, from the pFA6-hph-NT1 vector.

2) Simulataneously add 42 bp nucleotide sequences homologous to regions surrounding ERG9 gene in yeast genome.

3) Purified PCR fragment is transformed into various cell lines identified in phase 2 with the ability to accumulate farnesol and selected on YPDE plates containing 300 mg/L hygromycin.

4) Independent single colonies are picked for ergosterol dependent test, PCR confirmation of recombination with hphF and ERG9 450DWR primer.

5) Farnesol production analysis done by GC-MS/LC-MS.

ERG1 Knockout Mutations

1) Primers ERG1F and ERG1R used to amplify the sqalene epoxidase synthase ERG1 gene by using Takara high fidelity Primerstar taq polymerase.

2) Obtained PCR fragment is gel purified, A tailed and ligated into the pGEM-Teasy vector.

3) Obtained vector is used as template to run second PCR with primers Ergl-splitF and EGR1-splitR to obtain PCR fragment with deletion of 891 bp CDS in the middle, yet containing 310 bp at 5' end region and 291 bp at 3' end region of ERG1 gene which are the target homologous recombination sequence for ERG1 knockout.

4) After digestion with BamHI, self-ligation, and transformation to DH5alpha competent cells, resulting vector is pGEM-ERG1-split.

5) Padh-Kanmx4-Tcyc-LoxP antibiotic selection marker cassette is constructed by assembly PCR of three fragments.

6) Padh promoter is PCR amplified with Padh-loxP-ManHIF and Padh-Kanmx4R primers using Yep352 vector as a template.

7) Kanmx4 selection gene is PCR amplified using Padh-kanmx4F and Tcyc-kanmx4R primers using PYM-N14 plasmid as a template.

8) Tcyc terminator was PCR amplified with Padh-loxP-BamHIF and Padh-Kanmx4R primers using Pesc vector as a template.

9) 3 PCR fragments containing homologous regions with each other were gel purified and 250 ng of each fragment were mixed together to serve as template for the secondary assembly PCR reaction to yield pAdh-Kanmx4-Tcyc-LoxP cassette.

10) Cassette is digested and inserted into pGEM-ERG1-split vector, and used as template to run PCR with ERG1F and ERG1R to get PCR fragment used to generate cell lines.

11) Pgpd-tHMGR-Tadh fragment was amplified from Pesc-Gpd-leu-tHMGR vector with primers GPD-BamHIP and Tadh-XhoIIR.

12) Insert fragment into pGEM-ERG1-split vector containing kanmx4 cassette.

13) Use construct as template to amplify with ERG1F and EGR1R primers to gain the fragment for building slightly different cell lines, which include integration of one copy of tHMGR into the ERG1 gene.

| Primer Name | Primer Sequence |
|---|---|
| ERG9pS1 (SEQ ID NO: 1) | TACATTTCATAGCCCATCTTCAACAAC AATACCGACTTACCCGTACGCTGCAGG TCGAC |
| ERG9 250dwS2 (SEQ ID NO: 2) | CAGATTGACGGAGAGAGGGCCACATTG TTTGTCGGCAATAAATCGATGAATTCG AGCTCG |
| Hph F (SEQ ID NO: 3) | ATGGGTAAAAAGCCTGAACTCA |
| Hph R (SEQ ID NO: 4) | TTATTCCTTTGCCCTCGGACGAG |
| ERG9 450dwR (SEQ ID NO: 5) | AGATGCTAGTCAATGGCAGAAG |
| ERG9p300upF (SEQ ID NO: 6) | TGCTTACACAGAGTGAACCTGC |
| ERG9 300R (SEQ ID NO: 7) | CTCGTGGAAGTGACGCAAC |
| pGPD-BamHI F (SEQ ID NO: 8) | cgGGATCCAgtttatcattatcaatac tcgcc |
| pGPD-NotIR (SEQ ID NO: 9) | gggGCGGCCGCgagctcagtdatcatt atc |
| tHMGR-NotIF (SEQ ID NO: 10) | GGGGCGGCCGCAAAACAATGTTGTCAC GACTTTTCCGTATGC |
| tHMGR-SpeIR (SEQ ID NO: 11) | GACTAGT TCAAGCTGACTTCTTGGTG CACGTTCCTTG |
| ERG1F (SEQ ID NO: 12) | ATGTCTGCTGTTAACGTTGCACCTG |
| ERG1R (SEQ ID NO: 13) | TTAACCAATCAACTCACCAAAC |
| ERG1-split F (SEQ ID NO: 14) | CGGGATCCCTCGAG TTGTTCGCTGCT GACAGCGATAAC |
| ERG1-splitR (SEQ ID NO: 15) | CGGGATCCGCTAGCGGTACCACATGGG TCCTTTATATTGACACG |
| ERG1 90up F (SEQ ID NO: 16) | ATCAGAACAATTGTCCAGTATTG |
| ERG1100dwR (SEQ ID NO: 17) | AATGTACTATACAAGCCTTCC |
| bSQS-NotIF (SEQ ID NO: 18) | GGGGCGGCCGCAAAACAATGGGGATGC TTCGCTGGGGAGT |
| bSQS-SpeIR (SEQ ID NO: 19) | GACTAGTTTAGCTCCTCAATTCGTCAA AGGT |
| Cre-NotIF (SEQ ID NO: 20) | GGGGCGGCCGCAAAACAATGGACATGT TCAGGGATCGCCAGG |
| Cre-SpeIR (SEQ ID NO: 21) | GACTAGTCTAATCGCCATCTTCCAGCA GGCG |
| Padh-Loxp-BamHIF (SEQ ID NO: 22) | CGGGATCCATAACTTCGTATAGCATAC ATTATACGAAGTTATGTGGAATATTTC GGATAT |
| Padh-Kanmx4F (SEQ ID NO: 23) | GCATACAATCAACTAAGCTAAGCTAAA ACAATGGGTAAGGAAAAGACTCACGTT TC |
| Padh-Kanmx4R (SEQ ID NO: 24) | GAAACGTGAGTCTTTTCCTTACCCATT GTTTTAGCTTAGCTTAGTTGATTGTAT GC |
| Kanmx4-TcycF (SEQ ID NO: 25) | CATTTGATGCTCGATGAGTTTTTCTAA ATCCGCTCTAACCGAAAAGGAAGGAG |
| Kanmx4-TcycR (SEQ ID NO: 26) | CTCCTTCCTTTTCGGTTAGAGCGGATT TAGAAAAACTCATCGAGCATCAAATG |
| Tcyc-LoxP-NheIR (SEQ ID NO: 27) | GGGGCTAGCATAACTTCGTATAATGTA TGCTATACGAAGTTATCTTCGAGCGTC CCAAAA |
| Gpd-BamHIF (SEQ ID NO: 28) | CGGGATCCAGTTTATCATTATCAATAC TCG |
| Tadh-XhoIR (SEQ ID NO: 29) | GGGCTCGAG GAGCGACCTCATGCTAT ACCTG |
| Kanmx4R (SEQ ID NO: 30) | TTAGAAAACTCATCGAGCATC |

Expression of Enzymes for Cannabinoid Production

```
LS          5' FWD
Length:     55
Type:       DNA
Organism:   Artificial Sequence
Notes:      Primer
                                                            SEQ ID NO: 31
Gcatagcaatctaatctaagttttaaa atgaatcatttgagagcagaagggcctgc CB          5' FWD
Length:     56
Type:       DNA
Organism:   Artificial Sequence
Notes:      Primer
                                                            SEQ ID NO: 32
caccagaacttagtttcgacggataaa atggaaaccggtttgtcctcggtttgcac All REV
Length:     58
Type:       DNA
Organism:   Artificial Sequence
Notes:      Primer
                                                            SEQ ID NO: 33
cataactaattacatgatttaaccTTAAACATCAGATTCAATAGAGCCGCCTCCACTG Backbone |CBGA synthase |Flexible spacer |CBD synthase target peptide
Length:
Type:       DNA
Organism:   artificial sequence
Notes:      Codon optimized
                                                            SEQ ID NO: 34
   1        ggttaaatca tgtaattagt tatgtcacgc ttacattcac gccctccccc cacatccgct
  61        ctaaccgaaa aggaaggagt tagacaacct gaagtctagg tccctattta ttttttttata
 121        gttatgttag tattaagaac gttatttata tttcaaattt ttcttttttt tctgtacaga
 181        cgcgtgtacg catgtaacat tatactgaaa accttgcttg agaaggtttt gggacgctcg
 241        aaggctttaa tttgcggccc ctcacctgca cgcaaaatag gataattata ctctatttct
 301        caacaagtaa ttggttgttt ggccgagcgg tctaaggcgc ctgattcaag aaatatcttg
 361        accgcagtta actgtgggaa tactcaggta tcgtaagatg caagagttcg aatctcttag
 421        caaccattat tttttttcctc aacataacga gaacacacag gggcgctatc gcacagaatc
 481        aaattcgatg actggaaatt ttttgttaat ttcagaggtc gcctgacgca tataccttttt
 541        tcaactgaaa aattgggaga aaaggaaag gtgagagcgc cggaaccggc ttttcatata
 601        gaatagagaa gcgttcatga ctaaatgctt gcatcacaat acttgaagtt gacaatatta
 661        tttaaggacc tattgttttt tccaataggt ggttagcaat cgtcttactt tctaactttt
 721        cttacctttt acatttcagc aatatatata tatatatttc aaggatatac cattctaatg
 781        tctgccccta agaagatcgt cgttttgcca ggtgaccacg ttggtcaaga aatcacagcc
 841        gaagccatta aggttcttaa agctatttct gatgttcgtt ccaatgtcaa gttcgatttc
 901        gaaaatcatt taattggtgg tgctgctatc gatgctacag gtgttccact tccagatgag
 961        gcgctggaag cctccaagaa ggctgatgcc gttttgttag gtgctgtggg tggtcctaaa
1021        tggggtaccg gtagtgttag acctgaacaa ggtttactaa aaatccgtaa agaacttcaa
1081        ttgtacgcca acttaagacc atgtaacttt gcatccgact ctctttttaga cttatctcca
1141        atcaagccac aatttgctaa aggtactgac ttcgttgttg tcagagaatt agtgggaggt
1201        atttactttg gtaagagaaa ggaagatgat ggtgatggtg tcgcttggga tagtgaacaa
1261        tacaccgttc cagaagtgca aagaatcaca agaatggccg ctttcatggc cctacaacat
1321        gagccaccat tgcctatttg gtccttggat aaagctaatg ttttggcctc ttcaagatta
1381        tggagaaaaa ctgtggagga aaccatcaag aacgaattcc ctacattgaa ggttcaacat
1441        caattgattg attctgccgc catgatccta gttaagaacc caacccacct aaatggtatt
```

-continued

```
1501  ataatcacca gcaacatgtt tggtgatatc atctccgatg aagcctccgt tatcccaggt
1561  tccttgggtt tgttgccatc tgcgtccttg gcctctttgc cagacaagaa caccgcattt
1621  ggtttgtacg aaccatgcca cggttctgct ccagatttgc caaagaataa ggtcaaccct
1681  atcgccacta tcttgtctgc tgcaatgatg ttgaaattgt cattgaactt gcctgaagaa
1741  ggtaaggcca ttgaagatgc agttaaaaag gttttggatg caggcatcag aactggtgat
1801  ttaggtggtt ccaacagtac caccgaagtc ggtgatgctg tcgccgaaga agttaagaaa
1861  atccttgctt aaaaagattc tctttttta tgatatttgt acataaactt tataaatgaa
1921  attcataata gaaacgacac gaaattacaa aatggaatat gttcataggg taacgctatg
1981  atccaatatc aaaggaaatg atagcattga aggatgagac taatccaatt gaggagtggc
2041  agcatataga acagctaaag ggtagtgctg aaggaagcat acgataccCC gcatggaatg
2101  ggataatatc acaggaggta ctagactacc tttcatccta cataaataga cgcatataag
2161  tacgcattta agcataaaca cgcactatgc cgttcttctc atgtatatat atatacaggc
2221  aacacgcaga tataggtgcg acgtgaacag tgagctgtat gtgcgcagct cgcgttgcat
2281  tttcggaagc gctcgttttc ggaaacgctt tgaagttcct attccgaagt tcctattctc
2341  tagaaagtat aggaacttca gagcgctttt gaaaccaaa agcgctctga agtcgcactt
2401  tcaaaaaacc aaaaacgcac cggactgtaa cgagctacta aaatattgcg aataccgctt
2461  ccacaaacat tgctcaaaag tatctctttg ctatatatct ctgtgctata tccctatata
2521  acctacccat ccacctttcg ctccttgaac ttgcatctaa actcgacctc tacatttttt
2581  atgtttatct ctagtattac tctttagaca aaaaattgt agtaagaact attcatagag
2641  tgaatcgaaa acaatacgaa aatgtaaaca tttcctatac gtagtatata gagacaaaat
2701  agaagaaacc gttcataatt ttctgaccaa tgaagaatca tcaacgctat cactttctgt
2761  tcacaaagta tgcgcaatcc acatcggtat agaatataat cggggatgcc tttatcttga
2821  aaaaatgcac ccgcagcttc gctagtaatc agtaaacgcg ggaagtggag tcaggctttt
2881  tttatggaag agaaaataga caccaaagta gccttcttct aaccttaacg gacctacagt
2941  gcaaaaagtt atcaagagac tgcattatag agcgcacaaa ggagaaaaaa agtaatctaa
3001  gatgctttgt tagaaaaata gcgctctcgg gatgcatttt tgtagaacaa aaaagaagta
3061  tagattcttt gttggtaaaa tagcgctctc gcgttgcatt tctgttctgt aaaaatgcag
3121  ctcagattct tgtttgaaa aattagcgct ctcgcgttgc atttttgttt tacaaaaatg
3181  aagcacagat tcttcgttgg taaaatagcg ctttcgcgtt gcatttctgt tctgtaaaaa
3241  tgcagctcag attctttgtt tgaaaaatta gcgctctcgc gttgcatttt tgttctacaa
3301  aatgaagcac agatgcttcg ttcaggtggc acttttcggg gaaatgtgcg cggaacccct
3361  atttgtttat ttttctaaat acattcaaat atgtatccgc tcatgagaca ataaccctga
3421  tattggtcag aattggttaa ttggttgtaa cactgacccc tatttgttta tttttctaaa
3481  tacattcaaa tatgtatccg ctcatgagac aataaccctg ataaatgctt caataatatt
3541  gaaaaaggaa gaatatgagc catattcaac gggaaacgtc gaggccgcga ttaaattcca
3601  acatggatgc tgatttatat gggtataaat gggctcgcga taatgtcggg caatcaggtg
3661  cgacaatcta tcgcttgtat gggaagcccg atgcgccaga gttgttctg aaacatggca
3721  aaggtagcgt tgccaatgat gttacagatg agatggtcag actaaactgg ctgacggaat
3781  ttatgccact tccgaccatc aagcatttta tccgtactcc tgatgatgca tggttactca
3841  ccactgcgat ccccggaaaa acagcgttcc aggtattaga agaatatcct gattcaggtg
```

-continued

```
3901    aaaatattgt tgatgcgctg gcagtgttcc tgcgccggtt gcactcgatt cctgtttgta
3961    attgtccttt taacagcgat cgcgtatttc gcctcgctca ggcgcaatca cgaatgaata
4021    acggtttggt tgatgcgagt gattttgatg acgagcgtaa tggctggcct gttgaacaag
4081    tctggaaaga aatgcataaa cttttgccat tctcaccgga ttcagtcgtc actcatggtg
4141    atttctcact tgataacctt atttttgacg aggggaaatt aataggttgt attgatgttg
4201    gacgagtcgg aatcgcagac cgataccagg atcttgccat cctatggaac tgcctcggtg
4261    agttttctcc ttcattacag aaacggcttt tcaaaaata tggtattgat aatcctgata
4321    tgaataaatt gcaatttcat ttgatgctcg atgagttttt ctaactcatg accaaaatcc
4381    cttaacgtga gttacgcgcg cgtcgttcca ctgagcgtca gaccccgtag aaaagatcaa
4441    aggatcttct tgagatcctt ttttttctgcg cgtaatctgc tgcttgcaaa caaaaaaacc
4501    accgctacca gcggtggttt gtttgccgga tcaagagcta ccaactcttt ttccgaaggt
4561    aactggcttc agcagagcgc agataccaaa tactgttctt ctagtgtagc cgtagttagc
4621    ccaccacttc aagaactctg tagcaccgcc tacatacctc gctctgctaa tcctgttacc
4681    agtggctgct gccagtggcg ataagtcgtg tcttaccggg ttggactcaa gacgatagtt
4741    accggataag gcgcagcggt cgggctgaac ggggggttcg tgcacacagc ccagcttgga
4801    gcgaacgacc tacaccgaac tgagatacct acagcgtgag ctatgagaaa gcgccacgct
4861    tcccgaaggg agaaaggcgg acaggtatcc ggtaagcggc agggtcggaa caggagagcg
4921    cacgagggag cttccagggg gaaacgcctg gtatctttat agtcctgtcg ggtttcgcca
4981    cctctgactt gagcgtcgat ttttgtgatg ctcgtcaggg gggcggagcc tatggaaaaa
5041    cgccagcaac gcggcctttt tacggttcct ggccttttgc tggccttttg ctcacatgtt
5101    ctttcctgcg ttatcccctg attctgtgga taaccgtatt accgcctttg agtgagctga
5161    taccgctcgg ggtcgtgcag gtagtttatc attatcaata ctcgccattt caaagaatac
5221    gtaaataatt aatagtagtg attttcctaa ctttatttag tcaaaaaatt agccttttaa
5281    ttctgctgta acccgtacat gcccaaaata gggggcgggt tacacagaat atataacatc
5341    gtaggtgtct gggtgaacag tttattcctg gcatccacta aatataatgg agcccgcttt
5401    ttaagctggc atccagaaaa aaaagaatc ccagcaccaa atattgttt tcttcaccaa
5461    ccatcagttc ataggtccat tctcttagcg caactacaga aacaggggc acaaacaggc
5521    aaaaaacggg cacaacctca atggagtgat gcaaccagcc tggagtaaat gatgacacaa
5561    ggcaattgac ccacgcatgt atctatctca ttttcttaca ccttctatta ccttctgctc
5641    tctctgattt ggaaaaagct gaaaaaaaag gttgaaacca gttccctgaa attattcccc
5701    tacttgacta ataagtatat aaagacggta ggtattgatt gtaattctgt aaatctattt
5761    cttaaacttc ttaaattcta cttttatagt tagtcttttt tttagttta aaacaccaga
5821    acttagtttc gacggataaa atgaaaccg gtttgtcctc ggtttgcact ttctccttcc
5881    aaacaaacta tcatacactc ctgaacccgc acaataacaa tcccaaaact tccctgctgt
5941    gttataggca cccaaagaca ccaatcaaat actcctacaa taactttcca tctaagcatt
6001    gtagcacaaa aagtttccat ttgcaaaata agtgttccga atctctgtcc atcgccaaaa
6061    attccattag ggctgccact actaatcaaa ctgaaccacc agagtctgat aatcattctg
6121    tcgccacaaa gattctgaat tttgggaagg cttgttggaa gttacaaaga ccatatacaa
6161    ttattgcctt tacctcttgt gcctgtggtt tatttggtaa ggaactgttg cataatacaa
6241    atttaatatc ttggtcattg atggaaacgt tcaaagcatt ttttttctta gtcgctatcc
6301    tttgtattgc ttctttcacc accactatca accagattta cgacttacat attgacagaa
```

-continued

```
6361  ttaacaagcc agatttgcca ctggcttcgg gcgagatttc cgtcaatact gcctggatca
6421  tggaaacttc tattattgtt gccttgtttg gattgataat caccataaaa atggaaacta
6481  agggtggtcc attgtatatt ttcggttact gttttggtat cttcggggc atcgtctact
6541  ctgttcctcc attcagatgg aaacaaaatc cttccacagc attcctttg aacttcctgg
6601  cgcacattat aaccaacttt actttttatt atgcctccag agccgccctg gggctgccct
6661  ttgaattacg cccctccttt acattttac tggccttcat ggagaccaag tccatggaga
6721  ctggttctgc tctcgcgttg atcaaagatg cttccgatgt ggaaggtgac accaaatttg
6761  gtatatccac tttggccagc aagtatggtt ccaggaattt gaccctattt tgttctggta
6841  tcgtgctgct gtcttatgtt gcagccatct tggctggcat catttggcca caggctttca
6901  attcaaatgt tatggagacg ctgctctcgc atgctatttt ggcattttgg ttgattctac
6961  agacaagaga ttttgcttta accaattatg acccagaagc tggtagaaga ttttacgaat
7021  ttatggaaac atggaaatta tactatgctg aatatttagt gtacgttttc attggggcg
7081  gctccagcgc cggcggcggc tcttctgcgg gcggttggtc tcatccacaa tttgagaaag
7141  gtgggtcgtc tggcggcggc agcggggggcg ggtccggcgg ggggagcggc ggtatgaaat
7201  gttcgacctt ctctttttgg tttgtctgta aaataatttt ttttttcttc agctttaaca
7261  ttcaaaccag cattgcaaat ccaagagaaa atttcttgaa atgcttttca caatatatcc
7321  ccaataatgc tactaacttg aagctagttt atactcaaaa caacccttg tacatgtccg
7361  tgctcaactc caccattcac aacctaagat tcacttcaga cactacccca aaaccattag
7441  ttattgtgac accttctcac gtttcacata tccaaggtac tattttatgc tccaagaagg
7501  tcggcctgca aattagaact agatctggag gtcatgattc agaaggaatg tcttacatct
7561  ctcaagttcc atttgtgatt gtcgatttaa gaaatatgag gagcattaag atcgatgttc
7621  actcccaaac ggcatgggtt gaagccggtg ccaccttggg cgaagtttac tactgggtca
7681  acgagaagaa tgaaaactta tcactagccg caggttattg tccaactgtt tgtgctggtg
7741  gccatttcgg aggcggcggc tacggtcctc taatgagaaa ctacggctta gctgctgaca
7801  atatcatcga cgctcacttg gttaacgttc atggtaaagt tttagataga aaatctatgg
7861  gtgaggatct tttctgggct ttgagaggtg gcggcgcaga atcatttggc attatcgttg
7921  cttggaagat cagattggtg gctgtcccca agtctacaat gttttctgtg aagaaaatta
7961  tggaaatcca tgaattggtc aaactggtga ataaatggca aaacatagct tacaagtacg
8041  ataaagactt gctgttaatg acacatttta ttaccaggaa catcactgat aaccaaggca
8101  agaacaagac tgcaattcat acttattttt cctccgtttt tttgggtggt gtcgactccc
8161  tcgtggatct gatgaataaa tcattccctg aactaggtat taaaaaaacc gattgtagac
8221  aattgagttg gattgatacc atcatattct acagtggtgt tgttaattat gatactgaca
8281  acttcaacaa agaaatactg ctggaccgtt ccgccggcca gaatggtgct tttaaaatca
8341  agttggatta tgtgaaaaag cctattccag aatccgtatt tgttcaaata ttggaaaagc
8401  tgtatgaaga agacattggt gcaggcatgt acgctcttta tccttatggc ggcataatgg
8461  atgaaatttc tgaaagtgcc attcctttcc cacatagggc cgggatcctg tacgagttat
8521  ggtacatttg ttcatgggaa aagcaagaag ataatgaaaa acatttaaat tggataagaa
8561  atatttataa ttttatgact ccatacgtct ccaaaaaccc acgcctggca tatttgaatt
8641  acagagacct ggatattggc atcaatgatc ctaaaaaccc aaataattac actcaggcaa
8701  gaatatgggg tgaaaaatat ttcggcaaaa attttgatag gctggtcaag gttaaaacac
```

-continued

```
8761        tggttgatcc aaacaatttc tttagaaacg aacaatctat cccacctctg cctagacata 8821        gacacggcgg tggaagcagt ggaggcggct ctattgaatc tgatgtttaa tga
```

Backbone |OLS |Flexible spacer |OAC |target peptide
Length:
Type:       DNA
Organism:   artificial sequence
Notes:      Codon optimized

SEQ ID NO: 35

```
   1        ggttaaatca tgtaattagt tatgtcacgc ttacattcac gccctccccc cacatccgct 61        ctaaccgaaa aggaaggagt tagacaacct gaagtctagg tccctattta ttttttttata 121        gttatgttag tattaagaac gttatttata tttcaaattt ttctttttttt tctgtacaga 181        cgcgtgtacg catgtaacat tatactgaaa accttgcttg agaaggtttt gggacgctcg 241        aaggcttttaa tttgcggccc ctcacctgca cgcaaaaagc tttcaattc aattcatcat 301        ttttttttta ttctttttttt tgatttcggt ttcttgaaa ttttttttgat tcggtaatct 361        ccgaacagaa ggaagaacga aggaaggagc acagacttag attggtatat atacgcatat 421        gtagtgttga agaaacatga aattgcccag tattcttaac ccaactgcac agaacaaaaa 481        ccagcaggaa acgaagataa atcatgtcga agctacata taaggaacgt gctgctactc 541        atcctagtcc tgttgctgcc aagctattta atatcatgca cgaaaagcaa acaaacttgt 601        gtgcttcatt ggatgttcgt accaccaagg aattactgga gttagttgaa gcattaggtc 661        ccaaaatttg tttactaaaa acacatgtgg atatcttgac tgatttttcc atggagggca 721        cagttaagcc gctaaaggca ttatccgcca agtacaattt ttactcttc gaagatagaa 781        aatttgctga cattggtaat acagtcaaat tgcagtactc tgcgggtgta tacagaatag 841        cagaatgggc agacattacg aatgcacacg tgtggtggg cccaggtatt gttagcggtt 901        tgaagcaggc ggcagaagaa gtaacaaagg aacctagagg ccttttgatg ttagcagaat 961        tgtcatgcaa gggctcccta tctactggag aatatactaa gggtactgtt gacattgcga 1021        aaagcgacaa agattttgtt atcggcttta ttgctcaaag agacatgggt ggaagagatg 1081        aaggttacga ttggttgatt atgacacccg tgtgggttt agatgacaag ggagatgcat 1141        tgggtcaaca gtatagaacc gtggatgatg ttgtctctac aggatctgac attattattg 1201        ttggaagagg actatttgca aagggaaggg atgctaaggt agagggtgaa cgttacagaa 2161        aagcaggctg ggaagcatat ttgagaagat gcggccagca aaactaaaaa actgtattat 1321        aagtaaatgc atgtatacta aactcacaaa ttagagcttc aatttaatta tatcagttat 1381        tacccacgct atgatccaat atcaaaggaa atgatagcat tgaaggatga gactaatcca 1441        attgaggagt ggcagcatat agaacagcta aagggtagtg ctgaaggaag catacgatac 1501        cccgcatgga atgggataat atcacaggag gtactagact acctttcatc ctacataaat 1561        agacgcatat aagtacgcat ttaagcataa acacgcacta tgccgttctt tcatgtata 1621        tatatataca ggcaacacgc agatataggt gcgacgtgaa cagtgagctg tatgtgcgca 1681        gctcgcgttg cattttcgga agcgctcgtt ttcggaaacg ctttgaagtt cctattccga 1741        agttcctatt ctctagaaag tataggaact tcagagcgct tttgaaaacc aaaagcgctc 1801        tgaagtcgca ctttcaaaaa accaaaaacg caccggactg taacgagcta ctaaaatatt 1861        gcgaataccg cttccacaaa cattgctcaa aagtatctct ttgctatata tctctgtgct 1921        atatccctat ataacctacc catccacctt tcgctccttg aacttgcatc taaactcgac 1981        ctctacattt tttatgttta tctctagtat tactctttag acaaaaaat tgtagtaaga 2041        actattcata gagtgaatcg aaaacaatac gaaaatgtaa acatttccta tacgtagtat 2101        atagagacaa aatagaagaa accgttcata atttctgac caatgaagaa tcatcaacgc
```

-continued

```
2161  tatcactttc tgttcacaaa gtatgcgcaa tccacatcgg tatagaatat aatcggggat
2221  gcctttatct tgaaaaaatg cacccgcagc ttcgctagta atcagtaaac gcgggaagtg
2281  gagtcaggct ttttttatgg aagagaaaat agacaccaaa gtagccttct tctaacctta
2341  acggacctac agtgcaaaaa gttatcaaga gactgcatta tagagcgcac aaaggagaaa
2401  aaaagtaatc taagatgctt tgttagaaaa atagcgctct cgggatgcat ttttgtagaa
2461  caaaaaagaa gtatagattc tttgttggta aaatagcgct ctcgcgttgc atttctgttc
2521  tgtaaaaatg cagctcagat tctttgtttg aaaaattagc gctctcgcgt tgcattttg
2581  ttttacaaaa atgaagcaca gattcttcgt tggtaaaata gcgctttcgc gttgcatttc
2641  tgttctgtaa aaatgcagct cagattcttt gtttgaaaaa ttagcgctct cgcgttgcat
2701  ttttgttcta caaaatgaag cacagatgct tcgttcaggt ggcacttttc ggggaaatgt
2761  gcgcggaacc cctatttgtt tatttttcta aatacattca aatatgtatc cgctcatgag
2821  acaataaccc tgatattggt cagaattggt taattggttg taacactgac ccctatttgt
2881  ttatttttct aaatacattc aaatatgtat ccgctcatga caataaaacc ctgataaatg
2941  cttcaataat attgaaaaag gaagaatatg agtattcaac atttccgtgt cgcccttatt
3001  cccttttttg cggcattttg ccttcctgtt tttgctcacc cagaaacgct ggtgaaagta
3061  aaagatgctg aagatcagtt gggtgcacga gtgggttaca tcgaactgga tctcaacagc
3121  ggtaagatcc ttgagagttt tcgccccgaa gaacgttttc caatgatgag cacttttaaa
3181  gttctgctat gtggcgcggt attatcccgt attgacgccg ggcaagagca actcggtcgc
3241  cgcatacact attctcagaa tgacttggtt gagtactcac cagtcacaga aaagcatctt
3301  acggatggca tgacagtaag agaattatgc agtgctgcca taaccatgag tgataacact
3361  gcggccaact tacttctgac aacgatcgga ggaccgaagg agctaaccgc ttttttgcac
3421  aacatggggg atcatgtaac tcgccttgat cgttgggaac cggagctgaa tgaagccata
3481  ccaaacgacg agcgtgacac cacgatgcct gtagcgatgg caacaacgtt gcgcaaacta
3541  ttaactggcg aactacttac tctagcttcc cggcaacaat taatagactg gatggaggcg
3601  gataaagttg caggaccact tctgcgctcg gcccttccgg ctggctggtt tattgctgat
3661  aaatccggag ccggtgagcg tggttctcgc ggtatcatcg cagcgctggg gccagatggt
3721  aagccctccc gtatcgtagt tatctacacg acggggagtc aggcaactat ggatgaacga
3781  aatagacaga tcgctgagat aggtgcctca ctgattaagc attggtaact catgaccaaa
3841  atcccttaac gtgagttacg cgcgcgtcgt tccactgagc gtcagacccc gtagaaaaga
3901  tcaaaggatc ttcttgagat ccttttttttc tgcgcgtaat ctgctgcttg caaacaaaaa
3961  aaccaccgct accagcggtg gtttgtttgc cggatcaaga ctaccaact ctttttccga
4021  aggtaactgg cttcagcaga gcgcagatac caaatactgt tcttctagtg tagccgtagt
4081  tagcccacca cttcaagaac tctgtagcac cgcctacata cctcgctctg ctaatcctgt
4141  taccagtggc tgctgccagt ggcgataagt cgtgtcttac cgggttggac tcaagacgat
4201  agttaccgga taaggcgcag cggtcgggct gaacggggggt tcgtgcaca cagcccagct
4261  tggagcgaac gacctacacc gaactgagat acctacagcg tgagctatga gaaagcgcca
4321  cgcttcccga agggagaaag gcggacaggt atccggtaag cggcagggtc ggaacaggag
4381  agcgcacgag ggagcttcca gggggaaacg cctggtatct ttatagtcct gtcgggtttc
4441  gccacctctg acttgagcgt cgatttttgt gatgctcgtc aggggggcgg agcctatgga
4501  aaaacgccag caacgcggcc tttttacggt tcctggcctt ttgctggcct tttgctcaca
```

-continued

```
4561    tgttctttcc tgcgttatcc cctgattctg tggataaccg tattaccgcc tttgagtgag 4621    ctgataccgc tcggggtcgt gcaggtatag cttcaaaatg tttctactcc ttttttactc 4681    ttccagattt tctcggactc cgcgcatcgc cgtaccactt caaaacaccc aagcacagca 4741    tactaaattt cccctctttc ttcctctagg gtgtcgttaa ttacccgtac taaaggtttg 4801    gaaagaaaa aagtgaccgc ctcgtttctt tttcttcgtc gaaaaaggca ataaaaattt 4861    ttatcacgtt tcttttctt gaaatttttt tttttgatt ttttctctt tcgatgacct 4921    cccattgata tttaagttaa taaacggact tcaatttctc aagtttcagt ttcattttc 4981    ttgttctatt acaactttt ttacctcttg ctcattagaa agaaagcata gcaatctaat 5041    ctaagtttaa aatgaatcat ttgagagcag aagggcctgc ttccgtgctg ctattggta 5101    ccgccaatcc agaaaatatc ctgctgcagg acgaattccc agattactat tttagggtca 5161    ccaaatctga acatatgaca caattgaaag agaaattcag aaagatttgt gacaagtcca 5221    tgattaggaa aagaaattgt ttttgaatg aagaacactt gaagcaaat cctcgcctgg 5281    tggagcatga atgcaaact ttggatgcta gacaagacat gttggtggtg aagttccaa 5341    agctggggaa ggatgcctgt gccaaggcca ttaagaatg gggccaacca aaatccaaaa 5401    ttaccacct gatttcacc tccgcctcca ccactgatat gccaggtgca gactatcatt 5461    gtgctaaatt gttgggtttg tcccctccg tgaagagagt tatgatgtat caattaggtt 5521    gttatggcgg cggcaccgtt ctgagaattg ccaaagacat tgctgaaaac aataaaggtg 5581    cgcgcgtttt ggctgtttgt tgtgatatta tggcatgtt atttagaggt ccaagtgaaa 5641    gtgacttgga attgctagtg ggccaggcca tatttggtga tggtgccgct gctgtgatcg 5701    ttggtgctga gcctgatgaa tctgtcggtg aaagaccaat ttttgaactg gtttccactg 5761    gtcaaaccat tttgccaaat tcagaaggta ctattggcgg ccatatcaga gaagctggtt 5821    taatctttga tttgcacaag gatgtcccaa tgttaattc caataatatt gaaaaatgtt 5881    tgatcgaagc atttacccc atcggtattt ctgattggaa ttccatcttc tggattacac 5941    atcctggcgg taaagctatc ttagataaag ttgaggagaa gttgcattta aagtctgaca 6001    aatttgttga ttcaagacat gtcctgtctg agcacggtaa tatgtcttcc tcgaccgtct 6061    tgtttgtcat ggatgagttg aggaagaggt ccctggaaga aggcaagagc accaccggtg 6121    acggttttga gtgggggtc ctctttggat ttgggccagg cctgaccgta gaaagggttg 6181    ttgtccgctc ggtgccaatc aaatatgtg ggggtccag cgccggtggc gggagctccg 6241    cgggcggttg gtctcaccca caatttgaaa agggtggcag cagcggcggc ggctctggcg 6301    gaggctccgg cggggctcg gggggtatgg ctgtcaagca tctgatcgtg ctgaagttca 6361    aagatgaaat tactgaagcc caaaggagg aatttttcaa gacatatgtt aatttggtta 6421    acatcattcc agcaatgaaa gatgtttatt ggggtaagga cgttactcaa aaaataagg 6481    aagagggtta cactcatatt gttgaagtca ctttcgaatc cgtcgaaaca attcaagatt 6541    atattattca tccagctcat gttgggtttg gcgatgtgta cagatcattt tgggaaaaat 6601    tattgatttt tgactacaca ccaagaaaag gcggtggaag cagtggaggc ggctctattg 6661    aatctgatgt ttaatag
```

-continued

Overexpression of ERG8m HFA1, ERG 10, ERG13, tHMGR, HMGR,
ERG12, ERG8, IDI Genes (for higher levels of intermediates)
Same process as expression of Synthase expression, but with 3
copies expressed in yeast cells.
Backbone |GGPS1|2a protease |HMC-CoA reductase|flexible spacer
IDI1
Length:
Type:      DNA
Organism:  artificial sequence
Notes:     Codon optimized

SEQ ID NO: 36

```
   1   atggagaaga ctcaagaaac agtccaaaga attcttctag aaccctataa atacttactt
  61   cagttaccag gtaaacaagt gagaaccaaa ctttcacagg catttaatca ttggctgaaa
 121   gttccagagg acaagctaca gattattatt gaagtgacag aaatgttgca taatgccagt
 181   ttactcatcg atgatattga agacaactca aaactccgac gtggctttcc agtggcccac
 241   agcatctatg gaatcccatc tgtcatcaat tctgccaatt acgtgtattt ccttggcttg
 301   gagaaagtct taacccttga tcacccagat gcagtgaagc tttttacccg ccagcttttg
 361   gaactccatc agggacaagg cctagatatt tactggaggg ataattacac ttgtcccact
 421   gaagaagaat ataaagctat ggtgctgcag aaaacaggtg gactgtttgg attagcagta
 481   ggtctcatgc agttgttctc tgattacaaa gaagatttaa accgctact taatacactt
 541   gggctctttt tccaaattag ggatgattat gctaatctac actccaaaga atatagtgaa
 601   aacaaaagtt tttgtgaaga tctgacagag ggaaagttct catttcctac tattcatgct
 661   atttggtcaa ggcctgaaag cacccaggtg cagaatatct gcgccagag aacagaaaac
 721   atagatataa aaaaatactg tgtacattat cttgaggatg taggttcttt tgaatacact
 781   cgtaataccc ttaaagagct tgaagctaaa gcctataaac agattgatgc acgtggtggg
 841   aaccctgagc tagtagcctt agtaaaacac ttaagtaaga tgttcaaaga gaaaatgaa
 901   ggcggttctg gcagcggaga gggcagagga agtcttctaa catgcggtga cgtggaggag
 961   aatcccggcc ctaggtctgg cagcggagag ggcagaggaa gtcttctaac atgcggtgac
1021   gtggaggaga atcccggccc taggacacaa agaaagtcc cagacaattg ttgtagacgt
1081   gaacctatgc tggtcagaaa taaccagaaa tgtgattcag tagaggaaga gacagggata
1141   aaccgagaaa gaaaagttga ggttataaaa cccttagtgg ctgaaacaga taccccaaac
1201   agagctacat tgtgtggttg taactcctcc ttactcgata cttcatcagt actggtgaca
1261   caggaacctg aaattgaact tcccagggaa cctcggccta atgaagaatg tctacagata
1321   cttgggaatg cagagaaagg tgcaaaattc cttagtgatg ctgagatcat ccagttagtc
1381   aatgctaagc atatcccagc ctacaagttg gaaactctga tggaaactca tgagcgtggt
1441   gtatctattg ccgacagtt acttccaag aagctttcag aaccttcttc tctccagtac
1501   ctaccttaca gggattataa ttactccttg gtgatgggag cttgttgtga aatgttatt
1561   ggatatatgc ccatccctgt tggagtggca ggaccccttt gctagatga aaaagaattt
1621   caggttccaa tggcaacaac agaaggttgt cttgtggcca gcaccaatag aggctgcaga
1681   gcaataggtc ttggtggagg tgccagcagc cgagtccttg cagatgggat gactcgtggc
1741   ccagttgtgc gtcttccacg tgcttgtgac tctgcagaag tgaaagcctg gctcgaaaca
1801   tctgaagggt tcgcagtgat aaaggaggca tttgacagca ctagcagatt tgcacgtcta
1861   cagaaacttc atacaagtat agctggacgc aacctttata tccgtttcca gtccaggtca
1921   ggggatgcca tggggatgaa catgatttca aagggtacag agaaagcact ttcaaaactt
1981   cacgagtatt tccctgaaat gcagattcta gccgttagtg gtaactattg tactgacaag
2041   aaacctgctg ctataaattg gatagaggga agaggaaaat ctgttgtttg tgaagctgtc
```

```
                                                    -continued
2101        attccagcca aggttgtcag agaagtatta aagactacca cagaggctat gattgaggtc 2161        aacattaaca agaatttagt gggctctgcc atggctggga gcataggagg ctacaacgcc 2221        catgcagcaa acattgtcac cgccatctac attgcctgtg gacaggatgc agcacagaat 2281        gttggtagtt caaactgtat tactttaatg gaagcaagtg gtcccacaaa tgaagattta 2341        tatatcagct gcaccatgcc atctatagag ataggaacgg tgggtggtgg gaccaaccta 2401        ctacctcagc aagcctgttt gcagatgcta ggtgttcaag gagcatgcaa agataatcct 2461        ggggaaaatg cccggcagct tgcccgaatt gtgtgtggga ccgtaatggc tggggaattg 2521        tcacttatgg cagcattggc agcaggacat cttgtcaaaa gtcacatgat tcacaacagg 2581        tcgaagatca atttacaaga cctccaagga gcttgcacca agaagacagc cggctcagga 2641        ggttcttcag gactggaagt gctgtttcag ggcccgggtg gatctggcat gatgcctgaa 2701        ataaacacta accacctcga caagcaacag gttcaactcc tggcagagat gtgtatcctt 2761        attgatgaaa atgacaataa aattggagct gagaccaaga agaattgtca cctgaacgag 2821        aacattgaga aaggattatt gcatcgagct tttagtgtct tcttattcaa caccgaaaat 2881        aagcttctgc tacagcaaag atcagatgct aagattacct ttccaggttg ttttacgaat 2941        acgtgttgta gtcatccatt aagcaatcca gccgagcttg aggaaagtga cgcccttgga 3001        gtgaggcgag cagcacagag acggctgaaa gctgagctag gaattccctt ggaagaggtt 3061        cctccagaag aaattaatta tttaacacga attcactaca aagctcagtc tgatggtatc 3121        tggggtgaac atgaaattga ttcattttg ttggtgagga agaatgtaac tttgaatcca 3181        gatcccaatg agattaaaag ctattgttat gtgtcaaagg aagaactaaa agaacttctg 3241        aaaaaagcag ccagtggtga aattaagata acgccatggt ttaaaattat tgcagcgact 3301        tttctcttta aatggtggga taacttaaat catttgaatc agtttgttga ccatgagaaa 3361        atatacagaa tg
```

| TABLE 1 | |
|---|---|
| Compounds | Pharmacological Characteristics |
| Cannabinoids (FIG. 1 and 2) | |
| Cannabigerolic acid (CBGA) | Antibiotic (1) |
| Cannabigerolic acid monomethylether (CBGAM) | |
| Cannabigerol (CBG) | Antibiotic, antifungal, anti-inflammatory, analgesic (1) Partial agonist at CB1/CB2 receptors (2) |
| Cannabigerovarinic acid (CBGVA) | |
| Cannabigerovarin (CBGV) | |
| Cannabichromenic acid (CBCA) | |
| Cannabichromene (CBC) | Anti-inflammatory, antibiotic, antifungal, analgesic (1) |
| Cannabichromevarinic acid (CBCVA) | |
| Cannabichromevarin (CBCV) | |
| Cannabidiolic acid (CBDA) | Antibiotic |
| Cannabidiol (CBD) | Anxiolytic, antipsychotic, analgesic, anti-inflammatory, antioxidant, antispasmodic (1) Ant schizophrenic, antiepileptic, sleep-promoting, anti-oxidizing, anti-inflammatory, immunomodulation properties (2) |
| Cannabidiol monomethylether (CBDM) | |
| Cannabidiol-C4 (CBD-C4) | |
| Cannabidivarinic acid (CBDVA) | |
| Cannabidivarin (CBDV) | |
| Cannabidiorcol (CBD-C1) | |

| TABLE 1-continued | |
|---|---|
| Compounds | Pharmacological Characteristics |
| Tetrahydrocannabinolic acid A (THCA-A) | |
| Tetrahydrocannabinolic acid B (THCA-B) | |
| Delta-9-tetrahydrocannabinol (THC) | Euphoriant, analgesic, anti-inflammatory, antioxidant, antiemetic (1) |
| Delta-9-tetrahydrocannabinolic acid-C4 (THCA-C4) | |
| Delta-9-tetrahydrocannabinol-C4 (THC-C4) | |
| Delta-8-tetrahydrocannabivarin (D8-THCV) | Exhibit in vitro pharma properties similar to THCV, and both can antagonize THC; behave as agonists or antagonists in dose dependent manner (2) |
| Delta-9-tetrahydrocannabivarinic acid (THCVA) | |
| Delta-9-tetrahydrocannabivarin (THCV) | Analgesic, euphoriant (1) Strong antagonist of anandamide (due to interactions with non-CB1/2 receptors), neuromodulator (in animal and human organs), some affects |

TABLE 1-continued

| Compounds | Pharmacological Characteristics |
|---|---|
| | due to interaction with non CB1/CB2 receptors (2) |
| Delta-9-tetrahydrocannabiorcolic acid (THCA-C1) | |
| Delta-9-tetrahydrocannabiorcol (THC-C1) | |
| Delta-7-cis-iso-tetrahydrocannabivarin (D7-THCV) | |
| Delta-8-tetrahydrocannabinolic acid (D8-THCA) | |
| Delta-8-tetrahydrocannabinol (D8-THC) | Similar to THC (1) Several 1-O-methyl- and 1-deoxy-delta-8-THC analogs have high CB2 receptor affinity[JWH133, JWH359, trans-(6aR,10aR)-3-(1,1-dimethylhexyl)-1-O-methyl-delta-8-THC]; antiemetic effects similar to THC (2) |
| Cannabicyclolic acid (CBLA) | |
| Cannabicyclol (CBL) | |
| Cannabicyclovarin (CBLV) | |
| Cannabielsoic acid A (CBEA-A) | |
| Cannabielsoic acid B (CBEA-B) | |
| Cannabielsoin (CBE) | |
| Cannabinolic acid (CBNA) | |
| Cannabinol (CBN) | Sedative, antibiotic, anticonvulsant, anti-inflammatory (1) |
| Cannabinol methylether (CBNM) | |
| Cannabinol-C4 (CBN-C4) | |
| Cannabivarin (CBV) | |
| Cannabinol-C2 (CBN-C2) | |
| Cannabinol-C1 (CBN-C1) | |
| Cannabinodiol (CBND) | |
| Cannabinodivarin (CBVD) | |
| Cannabitriol (CBT) | |
| 10-Ethoxy-9-hydroxy-delta-6a-tetrahydrocannabinol | |
| 8,9-Dihydroxy-delta-6a-tetrahydrocannabinol | |
| Cannabitriolvarin (CBTV) | |
| Ethoxy-cannabitriolvarin (CBTVE) | |
| Dehydrocannabifuran (DCBF) | |
| Cannabifuran (CBF) | |
| Cannabichromanon (CBCN) | |
| Cannabicitran (CBT) | |
| 10-oxo-delta-6a-tetrahydrocannabinol (OTHC) | |
| Delta-9-cis-tetrahydrocannabinol (Cis-THC) | |
| 3,4,5,6-Tetrahydro-7-hydroxy-alpha-alpha-2-trimethyl-9-n-propyl-2,6-methano-2H-1-benzoxocin-5-methanol (OH-iso-HHCV) | |
| Cannabiripsol (CBR) | |
| Trihydroxy-delta-9-tetrahydrocannabinol (triOH-THC) | |
| Terpeses/Terpenoids | |
| Beta-Myrcene | Analgesic, anti-inflammatory, antibiotic, antimutagenic |
| d-Limonene | Immune potentiator, antidepressant, antimutagenic |
| Linalool | Sedative, antidepressant, anxiolytic, immune potentiator |
| Trans-Ocimene | |
| Beta-Pinene | |
| Alpha-Pinene | Anti-inflammatory, bronchodilator, stimulant, antibiotic, antineoplastic, AChE inhibitor |

TABLE 1-continued

| Compounds | Pharmacological Characteristics |
|---|---|
| Beta-Caryophyllene | Anti-inflammatory, cytoprotective, antimalarial, CB2 agonist |
| Delta-3-Carene | |
| Pulegone | AChE inhibitor, sedative, antipyretic |
| Trans-gamma-Bisabolene | |
| Trans-alpha-Farnesene | |
| Beta-Fenchol | |
| Beta-Phellandrene | |
| Alpha-Humulene | |
| Guajol | |
| Alpha-Gualene | |
| Alpha-Eudesmol | |
| Terpinolene | |
| Alpha-Selinene | |
| Alpha-Terpineol | Sedative, antibiotic, AChE inhibitor, antioxidant, antimalarial |
| Fenchone | |
| Camphene | |
| Cis-Sabinene hydrate | |
| Cis-Ocimene | |
| Beta-Eudesmol | |
| Beta-Selinene | |
| Alpha-trans-Bergamolene | |
| Gamma-Eudesmol | |
| Borneol | |
| Cis-beta-Farnescene | |
| Gamma-Curcumene | |
| Cis-gamma-Bisabolene | |
| Alpha-Thujene | |
| Epi-alpha-Bisabolol | |
| Ipsdienol | |
| Alpha-Yiangene | |
| Beta-Elemene | |
| Alpha-cis-Bergamontene | |
| Gamma-Muurolene | |
| Alpha-Cadinene | |
| Alpha-Longipinene | |
| Caryophyllene oxide | |
| Spermidine Alkaloids (FIG. 6) | |
| (+)-Cannabisativine | |
| Palustridine | |
| Palustrine | |
| Spermidine | |
| Anhydrocannabisativine | |
| Phenolic Amides and Lignanamides (FIG. 5) | |
| N-trans-Feruloyltyramine | |
| N-p-Coumaroyltyramine | |
| N-trans-Caffeoyltyramine | |
| Grossamide | |
| Cannabisin-A | |
| Cannabisin-B | |
| Cannabisin-C | |
| Cannabisin-D | |
| Cannabisin-E | |
| Cannabisin-F | |
| Cannabisin-G | |
| Phenylpropanoids and Flavonoids (FIG. 4) | |
| Apigenin | |
| Luteolin | |
| Kaempferol | |
| Quercetin | |
| Orientin | |
| Vitexin | |

TABLE 1-continued

| Compounds | Pharmacological Characteristics |
|---|---|
| Cannflavin A | Inhibit prostaglandin E2 in human rheumatoid synovial cells |
| Cannflavin B | Inhibit prostaglandin E2 in human rheumatoid synovial cells |
| Stilbenoids (FIG. 3) | |
| Cannabispiran | |
| Isocannabispiran | |
| Cannabistilbene-IIa | |
| Cannabistilbene-IIb | |
| Cannithrene-1 | |
| Cannithrene-2 | |
| Acetyl cannabispirol | |
| Alpha-cannabisporanol | |
| Canniprene | |
| Cannabispirone | |

TABLE 2

| (Starting Materials) | | |
|---|---|---|
| Sugar based concentrates (High Fructose Corn Syrup, Molasses) | Hemicellulose | Glycerol |
| Glucose | Xylose | Whey |
| Sucrose | Methanol | Biodiesel |
| Cellulose | Lactic Acid | Citrate |
| Ethanol | Lignin | Fructose |
| Succinic Acid | Arabinose | Biofuels |
| Biomass | Saccharose | Starch based products |
| Agricultural residue | Water hyacinth | Aquatic biomass |

What is claimed is:

1. A method for increasing production of a cannabinoid or cannabinoid precursor molecule, comprising:
    providing a genetically modified yeast cell comprising: (i) a codon optimized polynucleotide sequence expressing cannabinoid or cannabinoid precursor molecule producing enzymes, and (ii) a mutation to prevent or reduce endogenous sterol synthesis selected from the group consisting of: a SUE (sterol uptake exogenous) mutation and an ERG1 (Squalene monooxygenase) gene knockout; contacting the genetically modified yeast cell with a starting material; and
    culturing the genetically modified yeast cell under conditions in which the cannabinoid or cannabinoid precursor molecule is produced from the starting material,
    wherein the cannabinoid or cannabinoid precursor molecule is selected from the group consisting of: cannabigerolic acid (CBGA), cannabigerovarinic acid (CBGVA), cannabidiolic acid (CBDA), cannabidivarinic acid (CBDVA), tetrahydrocannabinolic acid (THCA), delta-9-tetrahydrocannabivarinic acid (THCVA), cannabichromenic acid (CBCA), cannabichromevarinic acid (CBCVA), cannabigerol (CBG), cannabigerovarin (CBGV), cannabidiol (CBD), cannabidivarin (CBDV), tetrahydrocannabinol (THC), delta-9-tetrahydrocannabivarin (THCV), cannabichromene (CBC), cannabichromevarin (CBCV), olivetol, olivetolic acid, divarinic acid, divarinol, isopentenyl pyrophosphate (IPP), geranyl diphosphate (GPP) and farnesyl pyrophosphate (FPP), and wherein the starting material is selected from the group consisting of: rice, soya, maize, wheat, beans, sugar beet, sugar cane, plant biomass, starch, cellulose, ethanol, lignocellulose, high fructose corn syrup, molasses, fatty acids, glycerol, lactic acid, whey and glucose.

2. The method of claim 1, wherein the cannabinoid or cannabinoid precursor molecule is selected from the group consisting of:
CBGA, CBGVA, CBDA, CBDVA, THCA, THCVA, CBCA, CBCVA, CBG, CBGV, CBD, CBDV, THC, THCV, CBC and CBCV, and wherein the codon optimized polynucleotide sequence is at least 95% identical to the nucleic acid sequence of SEQ ID NO: 34.

3. The method of claim 1, wherein the cannabinoid precursor molecule is olivetol, olivetolic acid, divarinic acid or divarinol, and wherein the codon optimized polynucleotide sequence is at least 95% identical to the nucleic acid sequence of SEQ ID NO: 35.

4. The method of claim 1, wherein the cannabinoid precursor molecule is IPP, GPP or FPP, and wherein the codon
optimized polynucleotide sequence is at least 95% identical to the nucleic acid sequence of SEQ ID NO: 36.

5. The method of claim 1, wherein the modified yeast cell is *Saccharomyces cerevisiae* or *Pichia pastoris*.

6. The method of claim 1, wherein the genetically modified yeast cell further comprises knockout of an ERG9 (Squalene synthase) gene.

7. The method of claim 1, wherein the genetically modified yeast cell further comprises an additional copy of a yeast gene selected from the group consisting of: ERG10 (Acetyl-CoA acetyltransferase), ERG13 (Hydroxymethylglutaryl-CoA synthase), ERG12 (Mevalonate kinase), IDI1 (Isopentenyl-diphosphate Delta-isomerase 1) and HFA1 (Acetyl-CoA carboxylase, mitochondrial).

8. The method of claim 1, wherein the cannabinoid or cannabinoid precursor molecule is selected from the group consisting of: TFICA, CBDA, CBGA, CBCA, TFICVA, CBDVA, CBGVA and CBCVA; and wherein the starting material comprises free fatty acids and further comprises either hexanoic acid when the cannabinoid or cannabinoid precursor molecule is selected from the group consisting of TFICA, CBDA, CBGA and CBCA, or butyric acid when the cannabinoid or cannabinoid precursor molecule is selected from the group consisting of THCVA, CBDVA, CBGVA and CBCVA.

9. The method of claim 8, wherein the modified yeast cell is *Pichia pastoris*, and wherein the starting material further comprises methanol.

10. The method of claim 9, wherein the modified yeast cell further comprises a knockout of PEP4 (Proteinase A), PRB1 (Proteinase B) or YPS1 (Aspartic proteinase 3) genes.

* * * * *

```
                        SEQUENCE LISTING

<160> NUMBER OF SEQ ID NOS: 36

<210> SEQ ID NO 1
<211> LENGTH: 60
<212> TYPE: DNA
<213> ORGANISM: Artificial Sequence
<220> FEATURE:
<223> OTHER INFORMATION: Synthetic: ERG9pS1

<400> SEQUENCE: 1
gtacatttca tagcccatct tcaacaacaa taccgactta cccgtacgct gcaggtcgac    60

<210> SEQ ID NO 2
<211> LENGTH: 60
<212> TYPE: DNA
<213> ORGANISM: Artificial Sequence
<220> FEATURE:
<223> OTHER INFORMATION: Synthetic: ERG9 250dwS2

<400> SEQUENCE: 2
cagattgacg gagagagggc cacattgttt gtcggcaata aatcgatgaa ttcgagctcg    60

<210> SEQ ID NO 3
<211> LENGTH: 22
<212> TYPE: DNA
<213> ORGANISM: Artificial Sequence
<220> FEATURE:
<223> OTHER INFORMATION: Synthetic: Hph F

<400> SEQUENCE: 3
atgggtaaaa agcctgaact ca                                             22

<210> SEQ ID NO 4
<211> LENGTH: 23
<212> TYPE: DNA
<213> ORGANISM: Artificial Sequence
<220> FEATURE:
<223> OTHER INFORMATION: Synthetic: Hph R

<400> SEQUENCE: 4
ttattccttt gccctcggac gag                                            23

<210> SEQ ID NO 5
<211> LENGTH: 22
<212> TYPE: DNA
<213> ORGANISM: Artificial Sequence
<220> FEATURE:
```

<223> OTHER INFORMATION: Synthetic: ERG9 450dwR

<400> SEQUENCE: 5
agatgctagt caatggcaga ag                                              22

<210> SEQ ID NO 6
<211> LENGTH: 22
<212> TYPE: DNA
<213> ORGANISM: Artificial Sequence
<220> FEATURE:
<223> OTHER INFORMATION: Synthetic: ERG9p300upF

<400> SEQUENCE: 6
tgcttacaca gagtgaacct gc                                              22

<210> SEQ ID NO 7
<211> LENGTH: 19
<212> TYPE: DNA
<213> ORGANISM: Artificial Sequence
<220> FEATURE:
<223> OTHER INFORMATION: Synthetic: ERG9 300R

<400> SEQUENCE: 7
ctcgtggaag tgacgcaac                                                  19

<210> SEQ ID NO 8
<211> LENGTH: 32
<212> TYPE: DNA
<213> ORGANISM: Artificial Sequence
<220> FEATURE:
<223> OTHER INFORMATION: Synthetic: pGPD-BamHI F

<400> SEQUENCE: 8
cgggatccag tttatcatta tcaatactcg cc                                   32

<210> SEQ ID NO 9
<211> LENGTH: 31
<212> TYPE: DNA
<213> ORGANISM: Artificial Sequence
<220> FEATURE:
<223> OTHER INFORMATION: Synthetic: pGPD-NotIR

<400> SEQUENCE: 9
ggggcggccg cgagctcagt ttatcattat c                                    31

<210> SEQ ID NO 10
<211> LENGTH: 42
<212> TYPE: DNA
<213> ORGANISM: Artificial Sequence
<220> FEATURE:
<223> OTHER INFORMATION: Synthetic: tHMGR-NotIF

<400> SEQUENCE: 10
ggggcggccg caaaacaatg ttgtcacgac ttttccgtat gc                        42

<210> SEQ ID NO 11
<211> LENGTH: 37
<212> TYPE: DNA
<213> ORGANISM: Artificial Sequence
<220> FEATURE:
<223> OTHER INFORMATION: Synthetic: tHMGR-SpeIR

<400> SEQUENCE: 11
gactagttca agctgacttc ttggtgcacg ttccttg                              37

```
<210> SEQ ID NO 12
<211> LENGTH: 25
<212> TYPE: DNA
<213> ORGANISM: Artificial Sequence
<220> FEATURE:
<223> OTHER INFORMATION: Synthetic: ERG1F

<400> SEQUENCE: 12
atgtctgctg ttaacgttgc acctg                                          25

<210> SEQ ID NO 13
<211> LENGTH: 22
<212> TYPE: DNA
<213> ORGANISM: Artificial Sequence
<220> FEATURE:
<223> OTHER INFORMATION: Synthetic: ERG1R

<400> SEQUENCE: 13
ttaaccaatc aactcaccaa ac                                             22

<210> SEQ ID NO 14
<211> LENGTH: 38
<212> TYPE: DNA
<213> ORGANISM: Artificial Sequence
<220> FEATURE:
<223> OTHER INFORMATION: Synthetic: ERG1-split F

<400> SEQUENCE: 14
cgggatccct cgagttgttc gctgctgaca gcgataac                            38

<210> SEQ ID NO 15
<211> LENGTH: 44
<212> TYPE: DNA
<213> ORGANISM: Artificial Sequence
<220> FEATURE:
<223> OTHER INFORMATION: Synthetic: ERG1-splitR

<400> SEQUENCE: 15
cgggatccgc tagcggtacc acatgggtcc tttatattga cacg                     44

<210> SEQ ID NO 16
<211> LENGTH: 23
<212> TYPE: DNA
<213> ORGANISM: Artificial Sequence
<220> FEATURE:
<223> OTHER INFORMATION: Synthetic: ERG1 90up F

<400> SEQUENCE: 16
atcagaacaa ttgtccagta ttg                                            23

<210> SEQ ID NO 17
<211> LENGTH: 21
<212> TYPE: DNA
<213> ORGANISM: Artificial Sequence
<220> FEATURE:
<223> OTHER INFORMATION: Synthetic: ERG1100dwR

<400> SEQUENCE: 17
aatgtactat acaagccttc c                                              21

<210> SEQ ID NO 18
<211> LENGTH: 40
<212> TYPE: DNA
<213> ORGANISM: Artificial Sequence
<220> FEATURE:
<223> OTHER INFORMATION: Synthetic: bSQS-NotIF
```

<400> SEQUENCE: 18
ggggcggccg caaaacaatg gggatgcttc gctggggagt                                40

<210> SEQ ID NO 19
<211> LENGTH: 31
<212> TYPE: DNA
<213> ORGANISM: Artificial Sequence
<220> FEATURE:
<223> OTHER INFORMATION: Synthetic: bSQS-SpeIR

<400> SEQUENCE: 19
gactagttta gctcctcaat tcgtcaaagg t                                         31

<210> SEQ ID NO 20
<211> LENGTH: 42
<212> TYPE: DNA
<213> ORGANISM: Artificial Sequence
<220> FEATURE:
<223> OTHER INFORMATION: Synthetic: Cre-NotIF

<400> SEQUENCE: 20
ggggcggccg caaaacaatg gacatgttca gggatcgcca gg                             42

<210> SEQ ID NO 21
<211> LENGTH: 31
<212> TYPE: DNA
<213> ORGANISM: Artificial Sequence
<220> FEATURE:
<223> OTHER INFORMATION: Synthetic: Cre-SpeIR

<400> SEQUENCE: 21
gactagtcta atcgccatct tccagcaggc g                                         31

<210> SEQ ID NO 22
<211> LENGTH: 60
<212> TYPE: DNA
<213> ORGANISM: Artificial Sequence
<220> FEATURE:
<223> OTHER INFORMATION: Synthetic: Padh-Loxp-BamHIF

<400> SEQUENCE: 22
cgggatccat aacttcgtat agcatacatt atacgaagtt atgtggaata tttcggatat         60

<210> SEQ ID NO 23
<211> LENGTH: 56
<212> TYPE: DNA
<213> ORGANISM: Artificial Sequence
<220> FEATURE:
<223> OTHER INFORMATION: Synthetic: Padh-Kanmx4F

<400> SEQUENCE: 23
gcatacaatc aactaagcta agctaaaaca atgggtaagg aaaagactca cgtttc             56

<210> SEQ ID NO 24
<211> LENGTH: 56
<212> TYPE: DNA
<213> ORGANISM: Artificial Sequence
<220> FEATURE:
<223> OTHER INFORMATION: Synthetic: Padh-Kanmx4R

<400> SEQUENCE: 24
gaaacgtgag tcttttcctt acccattgtt ttagcttagc ttagttgatt gtatgc             56

<210> SEQ ID NO 25
<211> LENGTH: 53

```
<212> TYPE: DNA
<213> ORGANISM: Artificial Sequence
<220> FEATURE:
<223> OTHER INFORMATION: Synthetic: Kanmx4-TcycF

<400> SEQUENCE: 25
catttgatgc tcgatgagtt tttctaaatc cgctctaacc gaaaaggaag gag        53

<210> SEQ ID NO 26
<211> LENGTH: 53
<212> TYPE: DNA
<213> ORGANISM: Artificial Sequence
<220> FEATURE:
<223> OTHER INFORMATION: Synthetic: Kanmx4-TcycR

<400> SEQUENCE: 26
ctccttcctt ttcggttaga gcggatttag aaaaactcat cgagcatcaa atg        53

<210> SEQ ID NO 27
<211> LENGTH: 60
<212> TYPE: DNA
<213> ORGANISM: Artificial Sequence
<220> FEATURE:
<223> OTHER INFORMATION: Synthetic: Tcyc-LoxP-NheIR

<400> SEQUENCE: 27
ggggctagca taacttcgta taatgtatgc tatacgaagt tatcttcgag cgtcccaaaa   60

<210> SEQ ID NO 28
<211> LENGTH: 30
<212> TYPE: DNA
<213> ORGANISM: Artificial Sequence
<220> FEATURE:
<223> OTHER INFORMATION: Synthetic: Gpd-BamHIF

<400> SEQUENCE: 28
cgggatccag tttatcatta tcaatactcg                                    30

<210> SEQ ID NO 29
<211> LENGTH: 31
<212> TYPE: DNA
<213> ORGANISM: Artificial Sequence
<220> FEATURE:
<223> OTHER INFORMATION: Synthetic: Tadh-XhoIR

<400> SEQUENCE: 29
gggctcgagg agcgacctca tgctatacct g                                  31

<210> SEQ ID NO 30
<211> LENGTH: 22
<212> TYPE: DNA
<213> ORGANISM: Artificial Sequence
<220> FEATURE:
<223> OTHER INFORMATION: Synthetic: Kanmx4R

<400> SEQUENCE: 30
ttagaaaaac tcatcgagca tc                                            22

<210> SEQ ID NO 31
<211> LENGTH: 55
<212> TYPE: DNA
<213> ORGANISM: Artificial Sequence
<220> FEATURE:
<223> OTHER INFORMATION: Synthetic: OLS 5' FWD

<400> SEQUENCE: 31
```

```
gcatagcaat ctaatctaag tttaaaatga atcatttgag agcagaaggg cctgc        55
```

<210> SEQ ID NO 32
<211> LENGTH: 56
<212> TYPE: DNA
<213> ORGANISM: Artificial Sequence
<220> FEATURE:
<223> OTHER INFORMATION: Synthetic: CB 5' FWD

<400> SEQUENCE: 32

```
caccagaact tagtttcgac ggataaaatg gaaaccggtt tgtcctcggt ttgcac        56
```

<210> SEQ ID NO 33
<211> LENGTH: 58
<212> TYPE: DNA
<213> ORGANISM: Artificial Sequence
<220> FEATURE:
<223> OTHER INFORMATION: Synthetic: All REV

<400> SEQUENCE: 33

```
cataactaat tacatgattt aaccttaaac atcagattca atagagccgc ctccactg     58
```

<210> SEQ ID NO 34
<211> LENGTH: 8873
<212> TYPE: DNA
<213> ORGANISM: Artificial Sequence
<220> FEATURE:
<223> OTHER INFORMATION: Synthetic

<400> SEQUENCE: 34

```
ggttaaatca tgtaattagt tatgtcacgc ttacattcac gccctccccc cacatccgct     60
ctaaccgaaa aggaaggagt tagacaacct gaagtctagg tccctattta ttttttttata   120
gttatgttag tattaagaac gttatttata tttcaaattt ttcttttttt tctgtacaga   180
cgcgtgtacg catgtaacat tatactgaaa accttgcttg agaaggtttt gggacgctcg   240
aaggctttaa tttgcggccc ctcacctgca cgcaaaatag gataattata ctctatttct   300
caacaagtaa ttggttgttt ggccgagcgg tctaaggcgc ctgattcaag aaatatcttg   360
accgcagtta actgtgggaa tactcaggta tcgtaagatg caagagttcg aatctcttag   420
caaccattat tttttttcctc aacataacga gaacacacag gggcgctatc gcacagaatc   480
aaattcgatg actggaaatt ttttgttaat ttcagaggtc gcctgacgca tataccttt    540
tcaactgaaa aattgggaga aaaggaaag gtgagagcgc cggaaccggc ttttcatata    600
gaatagagaa gcgttcatga ctaaatgctt gcatcacaat acttgaagtt gacaatatta   660
tttaaggacc tattgttttt tccaataggt ggttagcaat cgtcttactt tctaactttt   720
cttacctttt acatttcagc aatatatata tatatatttc aaggatatac cattctaatg   780
tctgccccta agaagatcgt cgttttgcca ggtgaccacg ttggtcaaga atcacagcc    840
gaagccatta aggttcttaa agctatttct gatgttcgtt ccaatgtcaa gttcgatttc   900
gaaaatcatt taattggtgg tgctgctatc gatgctacag gtgttccact tccagatgag   960
gcgctggaag cctccaagaa ggctgatgcc gttttgttag gtgctgtggg tggtcctaaa  1020
tggggtaccg gtagtgttag acctgaacaa ggtttactaa aaatccgtaa agaacttcaa  1080
ttgtacgcca acttaagacc atgtaacttt gcatccgact ctcttttaga cttatctcca  1140
atcaagccac aatttgctaa aggtactgac ttcgttgttg tcagagaatt agtgggaggt  1200
atttactttg gtaagagaaa ggaagatgat ggtgatggtg tcgcttggga tagtgaacaa  1260
tacaccgttc cagaagtgca aagaatcaca agaatggccg ctttcatggc cctacaacat  1320
```

```
gagccaccat tgcctatttg gtccttggat aaagctaatg ttttggcctc ttcaagatta      1380
tggagaaaaa ctgtggagga aaccatcaag aacgaattcc ctacattgaa ggttcaacat      1440
caattgattg attctgccgc catgatccta gttaagaacc caacccacct aaatggtatt      1500
ataatcacca gcaacatgtt tggtgatatc atctccgatg aagcctccgt tatcccaggt      1560
tccttgggtt tgttgccatc tgcgtccttg gcctctttgc cagacaagaa caccgcattt      1620
ggtttgtacg aaccatgcca cggttctgct ccagatttgc caaagaataa ggtcaaccct      1680
atcgccacta tcttgtctgc tgcaatgatg ttgaaattgt cattgaactt gcctgaagaa      1740
ggtaaggcca ttgaagatgc agttaaaaag ttttggatg caggcatcag aactggtgat       1800
ttaggtggtt ccaacagtac caccgaagtc ggtgatgctg tcgccgaaga agttaagaaa      1860
atccttgctt aaaaagattc tcttttttta tgatatttgt acataaactt tataaatgaa      1920
attcataata gaaacgacac gaaattacaa aatggaatat gttcataggg taacgctatg      1980
atccaatatc aaaggaaatg atagcattga aggatgagac taatccaatt gaggagtggc      2040
agcatataga acagctaaag ggtagtgctg aaggaagcat acgatacccc gcatggaatg      2100
ggataatatc acaggaggta ctagactacc tttcatccta cataaataga cgcatataag      2160
tacgcattta agcataaaca cgcactatgc cgttcttctc atgtatatat atatacaggc      2220
aacacgcaga tataggtgcg acgtgaacag tgagctgtat gtgcgcagct cgcgttgcat      2280
tttcggaagc gctcgttttc ggaaacgctt tgaagttcct attccgaagt tcctattctc      2340
tagaaagtat aggaacttca gagcgctttt gaaaaccaaa agcgctctga agtcgcactt      2400
tcaaaaaacc aaaacgcac cggactgtaa cgagctacta aaatattgcg aataccgctt       2460
ccacaaacat tgctcaaaag tatctctttg ctatatatct ctgtgctata tccctatata      2520
acctacccat ccacctttcg ctccttgaac ttgcatctaa actcgacctc tacatttttt      2580
atgtttatct ctagtattac tctttagaca aaaaaattgt agtaagaact attcatagag      2640
tgaatcgaaa acaatacgaa aatgtaaaca tttcctatac gtagtatata gagacaaaat      2700
agaagaaacc gttcataatt ttctgaccaa tgaagaatca tcaacgctat cactttctgt      2760
tcacaaagta tgcgcaatcc acatcggtat agaatataat cggggatgcc tttatcttga      2820
aaaaatgcac ccgcagcttc gctagtaatc agtaaacgcg ggaagtggag tcaggctttt      2880
tttatggaag agaaaataga caccaaagta gccttcttct aaccttaacg gacctacagt      2940
gcaaaaagtt atcaagagac tgcattatag agcgcacaaa ggagaaaaaa agtaatctaa      3000
gatgctttgt tagaaaaata gcgctctcgg gatgcatttt tgtagaacaa aaagaagta      3060 tagattcttt gttggtaaaa tagcgctctc gcgttgcatt tctgttctgt aaaaatgcag      3120
ctcagattct ttgtttgaaa aattagcgct ctcgcgttgc attttgttt tacaaaaatg       3180 aagcacagat tcttcgttgg taaaatagcg ctttcgcgtt gcatttctgt tctgtaaaaa      3240
tgcagctcag attctttgtt tgaaaaatta gcgctctcgc gttgcatttt tgttctacaa      3300
aatgaagcac agatgcttcg ttcaggtggc acttttcggg gaaatgtgcg cggaacccct      3360
atttgtttat ttttctaaat acattcaaat atgtatccgc tcatgagaca ataaccctga      3420
tattggtcag aattggttaa ttggttgtaa cactgacccc tatttgttta ttttctaaa       3480 tacattcaaa tatgtatccg ctcatgagac aataaccctg ataaatgctt caataatatt      3540 gaaaaggaa gaatatgagc catattcaac gggaaacgtc gaggccgcga ttaaattcca       3600
acatggatgc tgatttatat gggtataaat gggctcgcga taatgtcggg caatcaggtg      3660
```

-continued

```
cgacaatcta tcgcttgtat gggaagcccg atgcgccaga gttgtttctg aaacatggca     3720
aaggtagcgt tgccaatgat gttacagatg agatggtcag actaaactgg ctgacggaat     3780
ttatgccact tccgaccatc aagcatttta tccgtactcc tgatgatgca tggttactca     3840
ccactgcgat ccccggaaaa acagcgttcc aggtattaga agaatatcct gattcaggtg     3900
aaaatattgt tgatgcgctg gcagtgttcc tgcgccggtt gcactcgatt cctgtttgta     3960
attgtccttt taacagcgat cgcgtatttc gcctcgctca ggcgcaatca cgaatgaata     4020
acggtttggt tgatgcgagt gattttgatg acgagcgtaa tggctggcct gttgaacaag     4080
tctggaaaga aatgcataaa cttttgccat tctcaccgga ttcagtcgtc actcatggtg     4140
atttctcact tgataacctt attttgacg aggggaaatt aataggttgt attgatgttg     4200
gacgagtcgg aatcgcagac cgataccagg atcttgccat cctatggaac tgcctcggtg     4260
agttttctcc ttcattacag aaacggcttt ttcaaaaata tggtattgat aatcctgata     4320
tgaataaatt gcaatttcat ttgatgctcg atgagttttt ctaactcatg accaaaatcc     4380
cttaacgtga gttacgcgcg cgtcgttcca ctgagcgtca gaccccgtag aaaagatcaa     4440
aggatcttct tgagatcctt ttttttctgcg cgtaatctgc tgcttgcaaa caaaaaaacc     4500
accgctacca gcggtggttt gtttgccgga tcaagagcta ccaactcttt ttccgaaggt     4560
aactggcttc agcagagcgc agataccaaa tactgttctt ctagtgtagc cgtagttagc     4620
ccaccacttc aagaactctg tagcaccgcc tacataccte gctctgctaa tcctgttacc     4680
agtggctgct gccagtggcg ataagtcgtg tcttaccggg ttggactcaa gacgatagtt     4740
accggataag gcgcagcggt cgggctgaac ggggggttcg tgcacacagc ccagcttgga     4800
gcgaacgacc tacaccgaac tgagatacct acagcgtgag ctatgagaaa gcgccacgct     4860
tcccgaaggg agaaaggcgg acaggtatcc ggtaagcggc agggtcggaa caggagagcg     4920
cacgagggag cttccagggg gaaacgcctg gtatctttat agtcctgtcg gtttcgcca     4980 cctctgactt gagcgtcgat ttttgtgatg ctcgtcaggg gggcggagcc tatggaaaaa     5040
cgccagcaac gcggccttt tacggttcct ggccttttgc tggccttttg ctcacatgtt     5100
ctttcctgcg ttatcccctg attctgtgga taaccgtatt accgcctttg agtgagctga     5160
taccgctcgg ggtcgtgcag gtagtttatc attatcaata ctcgccattt caagaatac     5220 gtaaataatt aatagtagtg attttcctaa ctttatttag tcaaaaaatt agccttttaa     5280
ttctgctgta acccgtacat gcccaaaata gggggcgggt tacacagaat atataacatc     5340
gtaggtgtct gggtgaacag tttattcctg gcatccacta aatataatgg agcccgcttt     5400
ttaagctggc atccagaaaa aaaagaatc ccagcaccaa aatattgttt tcttcaccaa     5460
ccatcagttc ataggtccat tctcttagcg caactacaga gaacaggggc acaaacaggc     5520
aaaaaacggg cacaacctca atggagtgat gcaaccagcc tggagtaaat gatgacacaa     5580
ggcaattgac ccacgcatgt atctatctca ttttcttaca ccttctatta ccttctgctc     5640
tctctgattt ggaaaaagct gaaaaaaaag gttgaaacca gttccctgaa attattcccc     5700
tacttgacta ataagtatat aaagacggta ggtattgatt gtaattctgt aaatctattt     5760
cttaaacttc ttaaattcta cttttatagt tagtctttt tttagtttta aacaccaga     5820 acttagtttc gacggataaa atggaaaccg gtttgtcctc ggtttgcact ttctccttcc     5880
aaacaaacta tcatacactc ctgaacccgc acaataacaa tcccaaaact tccctgctgt     5940
gttataggca cccaaagaca ccaatcaaat actcctacaa taactttcca tctaagcatt     6000
gtagcacaaa aagtttccat ttgcaaaata agtgttccga atctctgtcc atcgccaaaa     6060
```

```
attccattag ggctgccact actaatcaaa ctgaaccacc agagtctgat aatcattctg    6120
tcgccacaaa gattctgaat tttgggaagg cttgttggaa gttacaaaga ccatatacaa    6180
ttattgcctt tacctcttgt gcctgtggtt tatttggtaa ggaactgttg cataatacaa    6240
atttaatatc ttggtcattg atggaaacgt tcaaagcatt ttttttctta gtcgctatcc    6300
tttgtattgc ttctttcacc accactatca accagattta cgacttacat attgacagaa    6360
ttaacaagcc agatttgcca ctggcttcgg gcgagatttc cgtcaatact gcctggatca    6420
tggaaacttc tattattgtt gccttgtttg gattgataat caccataaaa atggaaacta    6480
agggtggtcc attgtatatt ttcggttact gttttggtat cttcggggge atcgtctact    6540 ctgttcctcc attcagatgg aaacaaaatc cttccacagc attccttttg aacttcctgg    6600
cgcacattat aaccaacttt acttttttatt atgcctccag agccgccctg gggctgccct    6660
ttgaattacg cccctccttt acattttttac tggccttcat ggagaccaag tccatggaga    6720
ctggttctgc tctcgcgttg atcaaagatg cttccgatgt ggaaggtgac accaaatttg    6780
gtatatccac tttggccagc aagtatggtt ccaggaattt gaccctattt tgttctggta    6840
tcgtgctgct gtcttatgtt gcagccatct tggctggcat catttggcca caggctttca    6900
attcaaatgt tatggagacg ctgctctcgc atgctatttt ggcattttgg ttgattctac    6960
agacaagaga ttttgcttta accaattatg acccagaagc tggtagaaga ttttacgaat    7020
ttatggaaac atgaaattta actatgctg aatatttagt gtacgttttc attggggggcg    7080 gctccagcgc cggcggcggc tcttctgcgg gcggttggtc tcatccacaa tttgagaaag    7140
gtgggtcgtc tggcggcggc agcgggggcg ggtccggcgg ggggagcggc ggtatgaaat    7200
gttcgacctt ctcttttttgg tttgtctgta aaataatttt ttttttcttc agctttaaca    7260
ttcaaaccag cattgcaaat ccaagagaaa atttcttgaa atgcttttca caatatatcc    7320
ccaataatgc tactaacttg aagctagttt atactcaaaa caacccttttg tacatgtccg    7380 tgctcaactc caccattcac aacctaagat tcacttcaga cactacccca aaaccattag    7440
ttattgtgac accttctcac gtttcacata tccaaggtac tatttatgc tccaagaagg    7500 tcggcctgca aattagaact agatctggag gtcatgattc agaaggaatg tcttacatct    7560
ctcaagttcc atttgtgatt gtcgatttaa gaaatgagg gagcattaag atcgatgttc    7620
actcccaaac ggcatgggtt gaagccggtg ccacctgggg cgaagtttac tactgggtca    7680
acgagaagaa tgaaaactta tcactagccg caggttattg tccaactgtt tgtgctggtg    7740
gccatttcgg aggcggcggc tacggtcctc taatgagaaa ctacggctta gctgctgaca    7800
atatcatcga cgctcacttg gttaacgttc atggtaaagt tttagataga aaatctatgg    7860
gtgaggatct tttctgggct ttgagaggtg gcggcgcaga atcatttggc attatcgttg    7920
cttggaagat cagattggtg gctgtcccca agtctacaat gttttctgtg aagaaaatta    7980
tggaaatcca tgaattggtc aaactggtga ataaatggca aaacatagct tacaagtacg    8040
ataaagactt gctgttaatg acacatttta ttaccaggaa catcactgat aaccaaggca    8100
agaacaagac tgcaattcat acttattttt cctccgttttt tttgggtggt gtcgactccc    8160
tcgtggatct gatgaataaa tcattccctg aactaggtat taaaaaaacc gattgtagac    8220
aattgagttg gattgatacc atcatattct acagtggtgt tgttaattat gatactgaca    8280
acttcaacaa agaaatactg ctggaccgtt ccgccggcca gaatggtgct tttaaaatca    8340
agttggatta tgtgaaaaag cctattccag aatccgtatt tgttcaaata ttggaaaagc    8400
```

```
tgtatgaaga agacattggt gcaggcatgt acgctcttta tccttatggc ggcataatgg      8460
atgaaatttc tgaaagtgcc attcctttcc cacatagggc cgggatcctg tacgagttat      8520
ggtacatttg ttcatgggaa aagcaagaag ataatgaaaa acatttaaat tggataagaa      8580
atatttataa ttttatgact ccatacgtct ccaaaaaccc acgcctggca tatttgaatt      8640
acagagacct ggatattggc atcaatgatc ctaaaaaccc aaataattac actcaggcaa      8700
gaatatgggg tgaaaaatat ttcggcaaaa attttgatag gctggtcaag gttaaaacac      8760
tggttgatcc aaacaatttc tttagaaacg aacaatctat cccacctctg cctagacata      8820
gacacggcgg tggaagcagt ggaggcggct ctattgaatc tgatgtttaa tga            8873

<210> SEQ ID NO 35
<211> LENGTH: 6677
<212> TYPE: DNA
<213> ORGANISM: Artificial Sequence
<220> FEATURE:
<223> OTHER INFORMATION: Synthetic

<400> SEQUENCE: 35
ggttaaatca tgtaattagt tatgtcacgc ttacattcac gccctccccc cacatccgct        60
ctaaccgaaa aggaaggagt tagacaacct gaagtctagg tccctattta ttttttttata     120 gttatgttag tattaagaac gttatttata tttcaaattt ttcttttttt tctgtacaga      180
cgcgtgtacg catgtaacat tatactgaaa accttgcttg agaaggtttt gggacgctcg      240
aaggctttaa tttgcggccc ctcacctgca cgcaaaaagc ttttcaattc aattcatcat      300 tttttttta ttctttttt tgatttcggt ttctttgaaa ttttttgat tcggtaatct         360 ccgaacagaa ggaagaacga aggaaggagc acagacttag attggtatat atacgcatat      420
gtagtgttga gaaacatga aattgcccag tattcttaac ccaactgcac agaacaaaaa       480
ccagcaggaa acgaagataa atcatgtcga aagctacata taaggaacgt gctgctactc      540
atcctagtcc tgttgctgcc aagctattta atatcatgca cgaaaagcaa acaaacttgt      600
gtgcttcatt ggatgttcgt accaccaagg aattactgga gttagttgaa gcattaggtc      660
ccaaaatttg tttactaaaa acacatgtgg atatcttgac tgatttttcc atggagggca     720
cagttaagcc gctaaaggca ttatccgcca agtacaattt tttactcttc gaagatagaa      780
aatttgctga cattggtaat acagtcaaat tgcagtactc tgcgggtgta tacagaatag      840
cagaatgggc agacattacg aatgcacacg tgtggtggg cccaggtatt gttagcggtt       900
tgaagcaggc ggcagaagaa gtaacaaagg aacctagagg cctttgatg ttagcagaat       960 tgtcatgcaa gggctcccta tctactggag aatatactaa gggtactgtt gacattgcga     1020
aaagcgacaa agattttgtt atcggcttta ttgctcaaag agacatgggt ggaagagatg     1080
aaggttacga ttggttgatt atgacacccg gtgtgggttt agatgacaag ggagatgcat     1140
tgggtcaaca gtatagaacc gtggatgatg ttgtctctac aggatctgac attattattg     1200
ttggaagagg actatttgca aagggaaggg atgctaaggt agagggtgaa cgttacagaa     1260
aagcaggctg ggaagcatat ttgagaagat gcggccagca aaactaaaaa actgtattat     1320
aagtaaatgc atgtatacta aactcacaaa ttagagcttc aatttaatta tatcagttat     1380
tacccacgct atgatccaat atcaaaggaa atgatagcat tgaaggatga gactaatcca     1440
attgaggagt ggcagcatat agaacagcta aagggtagtg ctgaaggaag catacgatac     1500
cccgcatgga atgggataat atcacaggag gtactagact acctttcatc ctacataaat     1560
agacgcatat aagtacgcat ttaagcataa acacgcacta tgccgttctt ctcatgtata     1620
```

```
tatatataca ggcaacacgc agatataggt gcgacgtgaa cagtgagctg tatgtgcgca   1680
gctcgcgttg cattttcgga agcgctcgtt ttcggaaacg ctttgaagtt cctattccga   1740
agttcctatt ctctagaaag tataggaact tcagagcgct tttgaaaacc aaaagcgctc   1800
tgaagtcgca ctttcaaaaa accaaaaacg caccggactg taacgagcta ctaaaatatt   1860
gcgaataccg cttccacaaa cattgctcaa aagtatctct ttgctatata tctctgtgct   1920
atatccctat ataacctacc catccacctt tcgctccttg aacttgcatc taaactcgac   1980
ctctacattt tttatgttta tctctagtat tactctttag acaaaaaaat tgtagtaaga   2040
actattcata gagtgaatcg aaaacaatac gaaaatgtaa acatttccta tacgtagtat   2100
atagagacaa aatagaagaa accgttcata attttctgac caatgaagaa tcatcaacgc   2160
tatcactttc tgttcacaaa gtatgcgcaa tccacatcgg tatagaatat aatcggggat   2220
gcctttatct tgaaaaaatg cacccgcagc ttcgctagta atcagtaaac gcgggaagtg   2280
gagtcaggct ttttttatgg aagagaaaat agacaccaaa gtagccttct tctaacctta   2340
acggacctac agtgcaaaaa gttatcaaga gactgcatta tagagcgcac aaaggagaaa   2400
aaaagtaatc taagatgctt tgttagaaaa atagcgctct cgggatgcat ttttgtagaa   2460 caaaaagaa gtatagattc tttgttggta aaatagcgct ctcgcgttgc atttctgttc   2520
tgtaaaaatg cagctcagat tctttgtttg aaaaattagc gctctcgcgt tgcattttg    2580 ttttacaaaa atgaagcaca gattcttcgt tggtaaaata gcgctttcgc gttgcatttc   2640
tgttctgtaa aaatgcagct cagattcttt gtttgaaaaa ttagcgctct cgcgttgcat   2700
ttttgttcta caaatgaag cacagatgct tcgttcaggt ggcacttttc ggggaaatgt    2760
gcgcggaacc cctatttgtt tattttcta aatacattca aatatgtatc cgctcatgag    2820
acaataaccc tgatattggt cagaattggt taattggttg taacactgac ccctatttgt   2880
ttatttttct aaatacattc aaatatgtat ccgctcatga caataaacc ctgataaatg     2940 cttcaataat attgaaaaag gaagaatatg agtattcaac atttccgtgt cgcccttatt   3000
cccttttttg cggcatttg ccttcctgtt tttgctcacc cagaaacgct ggtgaaagta     3060
aaagatgctg aagatcagtt gggtgcacga gtgggttaca tcgaactgga tctcaacagc   3120
ggtaagatcc ttgagagttt tcgccccgaa gaacgttttc caatgatgag cacttttaaa   3180
gttctgctat gtggcgcggt attatcccgt attgacgccg ggcaagagca actcggtcgc   3240
cgcatacact attctcagaa tgacttggtt gagtactcac cagtcacaga aaagcatctt   3300
acggatggca tgacagtaag agaattatgc agtgctgcca taaccatgag tgataacact   3360
gcggccaact tacttctgac aacgatcgga ggaccgaagg agctaaccgc ttttttgcac   3420
aacatggggg atcatgtaac tcgccttgat cgttgggaac cggagctgaa tgaagccata   3480
ccaaacgacg agcgtgacac cacgatgcct gtagcgatgg caacaacgtt gcgcaaacta   3540
ttaactggcg aactacttac tctagcttcc cggcaacaat taatagactg gatgaggcg    3600 gataaagttg caggaccact tctgcgctcg gcccttccgg ctggctggtt tattgctgat   3660
aaatccggag ccggtgagcg tggttctcgc ggtatcatcg cagcgctggg gccagatggt   3720
aagccctccc gtatcgtagt tatctacacg acggggagtc aggcaactat ggatgaacga   3780
aatagacaga tcgctgagat aggtgcctca ctgattaagc attggtaact catgaccaaa   3840
atcccttaac gtgagttacg cgcgcgtcgt tccactgagc gtcagacccc gtagaaaaga   3900
tcaaaggatc ttcttgagat cctttttttc tgcgcgtaat ctgctgcttg caaacaaaaa   3960
```

```
aaccaccgct accagcggtg gtttgtttgc cggatcaaga gctaccaact cttttttccga    4020
aggtaactgg cttcagcaga gcgcagatac caaatactgt tcttctagtg tagccgtagt    4080
tagcccacca cttcaagaac tctgtagcac cgcctacata cctcgctctg ctaatcctgt    4140
taccagtggc tgctgccagt ggcgataagt cgtgtcttac cgggttggac tcaagacgat    4200
agttaccgga taaggcgcag cggtcgggct gaacggggg ttcgtgcaca cagcccagct    4260
tggagcgaac gacctacacc gaactgagat acctacagcg tgagctatga aaagcgcca    4320
cgcttcccga agggagaaag gcggacaggt atccggtaag cggcagggtc ggaacaggag    4380
agcgcacgag ggagcttcca gggggaaacg cctggtatct ttatagtcct gtcgggtttc    4440
gccacctctg acttgagcgt cgattttttgt gatgctcgtc agggggggcgg agcctatgga    4500
aaaacgccag caacgcggcc ttttttacggt tcctggcctt ttgctggcct tttgctcaca    4560
tgttctttcc tgcgttatcc cctgattctg tggataaccg tattaccgcc tttgagtgag    4620
ctgataccgc tcggggtcgt gcaggtatag cttcaaaatg tttctactcc tttttttactc    4680
ttccagattt tctcggactc cgcgcatcgc cgtaccactc aaaacaccc aagcacagca    4740
tactaaattt cccctctttc ttcctctagg gtgtcgttaa ttaccgtac taaaggtttg    4800
gaaagaaaa aagtgaccgc ctcgtttctt tttcttcgtc gaaaaggca ataaaaattt    4860
ttatcacgtt tctttttctt gaaaattttt tttttttgatt tttttctctt tcgatgacct    4920
cccattgata tttaagttaa taaacggact tcaatttctc aagtttcagt ttcattttttc    4980
ttgttctatt acaactttttt ttacttcttg ctcattagaa agaaagcata gcaatctaat    5040
ctaagtttaa aatgaatcat ttgagagcag aagggcctgc ttccgtgctg gctattggta    5100
ccgccaatcc agaaaatatc ctgctgcagg acgaattccc agattactat tttagggtca    5160
ccaaatctga acatatgaca caattgaaag agaaattcag aaagatttgt gacaagtcca    5220
tgattaggaa aagaaattgt ttttttgaatg aagaacactt gaagcaaaat cctcgcctgg    5280
tggagcatga aatgcaaact ttggatgcta gacaagacat gttggtggtg gaagttccaa    5340
agctggggaa ggatgcctgt gccaaggcca ttaaagaatg gggccaacca aaatccaaaa    5400
ttacccacct gattttttcacc tccgcctcca ccactgatat gccaggtgca gactatcatt    5460
gtgctaaatt gttgggtttg tccccctccg tgaagagagt tatgatgtat caattaggtt    5520
gttatggcgg cggcaccgtt ctgagaattg ccaaagacat tgctgaaaac aataaaggtg    5580
cgcgcgtttt ggctgtttgt tgtgatatta tggcatgttt atttagaggt ccaagtgaaa    5640
gtgacttgga attgctagtg ggccaggcca tatttggtga tggtgccgct gctgtgatcg    5700
ttggtgctga gcctgatgaa tctgtcggtg aaagaccaat ttttgaactg gtttccactg    5760
gtcaaaccat tttgccaaat tcagaaggta ctattggcgg ccatatcaga gaagctggtt    5820
taatctttga tttgcacaag gatgtcccaa tgttaatttc caataatatt gaaaaatgtt    5880
tgatcgaagc atttacccccc atcggtattt ctgattggaa ttccatcttc tggattacac    5940
atcctggcgg taaagctatc ttagataaag ttgaggagaa gttgcattta aagtctgaca    6000
aatttgttga ttcaagacat gtcctgtctg agcacggtaa tatgtcttcc tcgaccgtct    6060
tgtttgtcat ggatgagttg aggaagaggt ccctggaaga aggcaagagc accaccggtg    6120
acggttttga gtgggggggtc ctctttggat ttgggccagg cctgaccgta gaaagggttg    6180
ttgtccgctc ggtgccaatc aaatatggtg gggggtccag cgccggtggc gggagctccg    6240
cggcggttg gtctcacccca caatttgaaa agggtgcag cagcggcggc ggctctggcg    6300
gaggctccgg cggggggctcg gggggtatgg ctgtcaagca tctgatcgtg ctgaagttca    6360
```

```
aagatgaaat tactgaagcc caaaaggagg aattttttcaa gacatatgtt aatttggtta    6420
acatcattcc agcaatgaaa gatgtttatt ggggtaagga cgttactcaa aaaaataagg    6480
aagagggtta cactcatatt gttgaagtca ctttcgaatc cgtcgaaaca attcaagatt    6540
atattattca tccagctcat gttgggtttg gcgatgtgta cagatcattt tgggaaaaat    6600
tattgatttt tgactacaca ccaagaaaag gcggtggaag cagtggaggc ggctctattg    6660
aatctgatgt ttaatag                                                   6677
```

<210> SEQ ID NO 36  
<211> LENGTH: 3372  
<212> TYPE: DNA  
<213> ORGANISM: Artificial Sequence  
<220> FEATURE:  
<223> OTHER INFORMATION: Synthetic

<400> SEQUENCE: 36

```
atggagaaga ctcaagaaac agtccaaaga attcttctag aaccctataa atacttactt      60
cagttaccag gtaaacaagt gagaaccaaa ctttcacagg catttaatca ttggctgaaa     120
gttccagagg acaagctaca gattattatt gaagtgacag aaatgttgca taatgccagt     180
ttactcatcg atgatattga agacaactca aaactccgac gtggctttcc agtggcccac     240
agcatctatg gaatcccatc tgtcatcaat tctgccaatt acgtgtattt ccttggcttg     300
gagaaagtct taacccttga tcacccagat gcagtgaagc ttttttacccg ccagcttttg     360 gaactccatc agggacaagg cctagatatt tactggaggg ataattacac ttgtcccact     420
gaagaagaat ataaagctat ggtgctgcag aaaacaggtg gactgtttgg attagcagta     480
ggtctcatgc agttgttctc tgattacaaa aagatttaa aaccgctact aatacactt     540 gggctctttt tccaaattag ggatgattat gctaatctac actccaaaga atatagtgaa     600
aacaaaagtt tttgtgaaga tctgacagag ggaaagttct catttcctac tattcatgct     660
atttggtcaa ggcctgaaag caccccaggtg cagaatatct tgcgccagag aacagaaaac     720
atagatataa aaaatactg tgtacattat cttgaggatg taggttcttt tgaatacact     780 cgtaatacce ttaaagagct tgaagctaaa gcctataaac agattgatgc acgtggtggg     840
aaccctgagc tagtagcctt agtaaaacac ttaagtaaga tgttcaaaga agaaaatgaa     900
ggcggttctg gcagcggaga gggcagagga agtcttctaa catgcggtga cgtggaggag     960
aatcccggcc taggtctgg cagcggagag ggcagaggaa gtcttctaac atgcggtgac    1020
gtggaggaga tcccggccc taggacacaa aagaaagtcc cagacaattg ttgtagacgt    1080
gaacctatgc tggtcagaaa taaccagaaa tgtgattcag tagaggaaga gacagggata    1140
aaccgagaaa gaaagttga ggttataaaa cccttagtgg ctgaaacaga taccccaaac    1200
agagctacat tgtggttgg taactcctcc ttactcgata cttcatcagt actggtgaca    1260
caggaacctg aaattgaact tcccagggaa cctcggccta atgaagaatg tctacagata    1320
cttgggaatg cagagaaagg tgcaaaattc cttagtgatg ctgagatcat ccagttagtc    1380
aatgctaagc atatcccagc ctacaagttg gaaactctga tggaaactca tgagcgtggt    1440
gtatctattc gccgacagtt actttccaag aagctttcag aaccttcttc tctccagtac    1500
ctaccttaca gggattataa ttactccttg gtgatgggag cttgttgtga aatgttatt    1560 ggatatatgc ccatccctgt tggagtggca ggacccctttt gcttagatga aaagaatttt    1620
caggttccaa tggcaacaac agaaggttgt cttgtggcca gcaccaatag aggctgcaga    1680
```

```
gcaataggtc ttggtggagg tgccagcagc cgagtccttg cagatgggat gactcgtggc    1740
ccagttgtgc gtcttccacg tgcttgtgac tctgcagaag tgaaagcctg gctcgaaaca    1800
tctgaagggt tcgcagtgat aaaggaggca tttgacagca ctagcagatt tgcacgtcta    1860
cagaaacttc atacaagtat agctggacgc aacctttata tccgtttcca gtccaggtca    1920
ggggatgcca tggggatgaa catgatttca aagggtacag agaaagcact ttcaaaactt    1980
cacgagtatt tccctgaaat gcagattcta gccgttagtg gtaactattg tactgacaag    2040
aaacctgctg ctataaattg gatagaggga agaggaaaat ctgttgtttg tgaagctgtc    2100
attccagcca aggttgtcag agaagtatta aagactacca cagaggctat gattgaggtc    2160
aacattaaca agaatttagt gggctctgcc atggctggga gcataggagg ctacaacgcc    2220
catgcagcaa acattgtcac cgccatctac attgcctgtg gacaggatgc agcacagaat    2280
gttggtagtt caaactgtat tactttaatg gaagcaagtg gtcccacaaa tgaagattta    2340
tatatcagct gcaccatgcc atctatagag ataggaacgg tgggtggtgg gaccaaccta    2400
ctacctcagc aagcctgttt gcagatgcta ggtgttcaag gagcatgcaa agataatcct    2460
ggggaaaatg cccggcagct tgcccgaatt gtgtgtggga ccgtaatggc tggggaattg    2520
tcacttatgg cagcattggc agcaggacat cttgtcaaaa gtcacatgat tcacaacagg    2580
tcgaagatca atttacaaga cctccaagga gcttgcacca agaagacagc cggctcagga    2640
ggttcttcag gactggaagt gctgtttcag ggcccgggtg gatctggcat gatgcctgaa    2700
ataaacacta accacctcga caagcaacag gttcaactcc tggcagagat gtgtatcctt    2760
attgatgaaa atgacaataa aattggagct gagaccaaga agaattgtca cctgaacgag    2820
aacattgaga aaggattatt gcatcgagct tttagtgtct tcttattcaa caccgaaaat    2880
aagcttctgc tacagcaaag atcagatgct aagattacct ttccaggttg ttttacgaat    2940
acgtgttgta gtcatccatt aagcaatcca gccgagcttg aggaaagtga cgcccttgga    3000
gtgaggcgag cagcacagag acggctgaaa gctgagctag gaattccctt ggaagaggtt    3060
cctccagaag aaattaatta tttaacacga attcactaca aagctcagtc tgatggtatc    3120
tggggtgaac atgaaattga ttacattttg ttggtgagga agaatgtaac tttgaatcca    3180
gatcccaatg agattaaaag ctattgttat gtgtcaaagg aagaactaaa agaacttctg    3240
aaaaaagcag ccagtggtga aattaagata acgccatggt ttaaaattat tgcagcgact    3300
tttctcttta aatggtggga taacttaaat catttgaatc agtttgttga ccatgagaaa    3360
atatacagaa tg                                                        3372
```